United States Patent [19]

Shiosaki et al.

[11] Patent Number: 5,338,726

[45] Date of Patent: Aug. 16, 1994

[54] ENDOTHELIN CONVERTING ENZYME INHIBITORS

[75] Inventors: Kazumi Shiosaki, Libertyville; Andrew S. Tasker, Lindenhurst, both of Ill.; Terry J. Opgenorth, Racine, Wis.

[73] Assignee: Abbott Laboratories, Abbott Park, Ill.

[21] Appl. No.: 954,403

[22] Filed: Sep. 29, 1992

Related U.S. Application Data

[63] Continuation of Ser. No. 696,487, May 6, 1991, abandoned, which is a continuation-in-part of Ser. No. 649,649, Jan. 31, 1991, abandoned.

[51] Int. Cl.$^5$ ............... A61K 37/02; C07K 5/06; C07K 5/08; C07K 5/10
[52] U.S. Cl. .......................... 514/17; 514/18; 514/19; 530/330; 530/331
[58] Field of Search ............... 530/330–331; 514/17–19

[56] References Cited

U.S. PATENT DOCUMENTS 4,855,286  8/1989  Wagner et al. ............ 514/19
4,981,950  1/1991  Masaki et al. ............ 530/326

*Primary Examiner*—Lester L. Lee
*Attorney, Agent, or Firm*—Steven R. Crowley

[57] ABSTRACT

Compounds are disclosed which inhibit endothelin converting enzyme. These compounds are useful for treating hypertension, congestive heart failure, myocardial infarction, reperfusion injury, coronary angina, cerebral vasospasm, acute renal failure, non-steroidal antiinflammatory drug induced gastric ulceration, cyclosporin induced nephrotoxicity, endotoxin-induced toxicity, asthma and atherosclerosis.

8 Claims, No Drawings

ENDOTHELIN CONVERTING ENZYME INHIBITORS

This is a continuation of U.S. patent application Ser. No. 696,487, filed May 6, 1991 and now abandoned, which is a continuation-in-part of U.S. patent application Ser. No. 649,649, filed Jan. 31, 1991 and now abandoned.

TECHNICAL FIELD

The present invention relates to compounds and compositions which inhibit endothelin converting enzyme (ECE), processes for making such compounds, synthetic intermediates employed in these processes and methods for suppressing endothelin production, treating hypertension, congestive heart failure, myocardial infarction, reperfusion injury, coronary angina, cerebral vasospasm, acute renal failure, non-steroidal antiinflammatory drug induced gastric ulceration, cyclosporin induced nephrotoxicity, endotoxin-induced toxicity, asthma and atherosclerosis with such compounds.

BACKGROUND ART

Endothelin (ET) is a 21 amino acid peptide that is produced by endothelial cells. ET is produced by enzymatic cleavage of a Trp-Val bond in the precursor peptide big endothelin (Big ET). This cleavage is caused by an endothelin converting enzyme (ECE). Endothelin has been shown to constrict arteries and veins, increase mean arterial blood pressure, decrease cardiac output, increase cardiac contractility in vitro, stimulate mitogenesis in vascular smooth muscle cells in vitro, contract nonvascular smooth muscle including guinea pig trachea, human urinary bladder strips and rat uterus in vitro, increase airway resistance in vivo, induce formation of gastric ulcers, stimulate release of atrial natriuretic factor in vitro and in vivo, increase plasma levels of vasopressin, aldosterone and catecholamines, inhibit release of renin in vitro and stimulate release of gonadotropins in vitro.

An agent which suppresses endothelin production or an agent which binds to endothelin would be expected to produce beneficial effects in a variety of therapeutic areas. In fact, an anti-endothelin antibody has been shown, upon intrarenal infusion, to ameliorate the adverse effects of renal ischemia on renal vascular resistance and glomerular filtration rate (Kon, et al., J. Clin. Invest. 83 1762 (1989)). In addition, an anti-endothelin antibody attenuated the nephrotoxic effects of intravenously administered cyclosporin (Kon, et al., Kidney Int. 37 1487 (1990)) and attenuated infarct size in a coronary artery ligation-induced myocardial infarction model (Watanabe, et al., Nature 344 114 (1990)).

An endothelin converting enzyme has been reported which can be inhibited by pepstatin A (Wu-Wong, et al., Biochem. Biophys. Res. Commun. 171 1291 (1990)). However, no other inhibitors of this endothelin converting enzyme are known.

DISCLOSURE OF THE INVENTION

In accordance with the present invention there are endothelin converting enzyme inhibiting compounds of the formula (I):

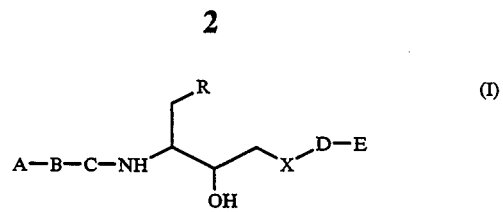

wherein
A is hydrogen, an N-protecting group or $R_1NHCH(R_2)C(O)$— wherein $R_1$ is H or an N-protecting group and $R_2$ is hydrogen, loweralkyl, cycloalkyl, cycloalkylalkyl, carboxyalkyl or alkoxycarbonylalkyl; or A is $HO_2C(CH_2)_nC(O)$— wherein n is 1 to 3;

B is —$N(R_4)CH(R_3)C(O)$— wherein $R_4$ is hydrogen or loweralkyl and $R_3$ is loweralkyl, cycloalkyl or cycloalkylalkyl;

C is —$N(R_5)CH(R_6)C(O)$— wherein $R_5$ is hydrogen or loweralkyl and $R_6$ is hydrogen, loweralkyl, cycloalkyl or cycloalkylalkyl;

R is loweralkyl, cycloalkyl, cycloalkylalkyl, aryl or bicyclic heterocyclic;

X is —$CH_2$— or —$C(O)$—;

D is
1) —$OR_7$ wherein $R_7$ is hydrogen, loweralkyl, cycloalkyl or cycloalkylalkyl;
2) —$NR_8R_9$ wherein $R_8$ and $R_9$ are independently selected from hydrogen, loweralkyl, cycloalkyl, cycloalkylalkyl and —$(CH_2)_m$—Z wherein m is 2 to 8 and Z is —OH, heterocyclic, —$SO_3H$, —$CO_2R_{10}$ wherein $R_{10}$ is hydrogen or loweralkyl or Z is —$NR_{11}R_{12}$ wherein $R_{11}$ and $R_{12}$ are independently selected from hydrogen, loweralkyl, cycloalkyl and cycloalkylalkyl;
(3) —$NHCH(R_{13})C(O)$— wherein $R_{13}$ is hydrogen, loweralkyl, cycloalkyl or cycloalkylalkyl; or
(4) —$NHCH(R_{13})C(O)NHCH(R_{14})C(O)$— wherein $R_{13}$ is hydrogen, loweralkyl, cycloalkyl or cycloalkylalkyl and $R_{14}$ is hydrogen, loweralkyl, cycloalkyl, cycloalkylalkyl, aminocarbonylalkyl, cyanoalkyl, carboxyalkyl or alkoxycarbonylalkyl; and E is
(1) absent;
(2) —$OR_{15}$ wherein $R_{15}$ is hydrogen, loweralkyl, cycloalkyl or cycloalkylalkyl; or
(3) —$NR_{16}R_{17}$ wherein $R_{16}$ and $R_{17}$ are independently selected from hydrogen, loweralkyl, cycloalkyl, cycloalkylalkyl and —$(CH_2)_p$—Y wherein p is 2 to 8 and Y is —OH, heterocyclic, —$SO_3H$, —$CO_2R_{18}$ wherein $R_{18}$ is hydrogen or loweralkyl or Y is —$NR_{19}R_{20}$ wherein $R_{19}$ and $R_{20}$ are independently selected from hydrogen, loweralkyl, cycloalkyl and cycloalkylalkyl; or a pharmaceutically acceptable salt, ester or prodrug thereof.

In accordance with the present invention there are also endothelin converting enzyme inhibiting compounds of the formula (II):

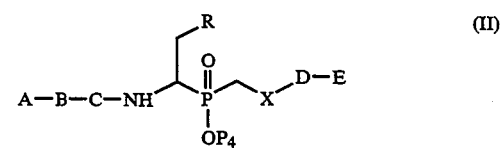

wherein

A is hydrogen, an N-protecting group, $R_1NHCH(R_2)C(O)$— wherein $R_1$ is H or an N-protecting group and $R_2$ is hydrogen, loweralkyl, cycloalkyl, cycloalkylalkyl, carboxyalkyl or alkoxycarbonylalkyl; or A is $HO_2C\ (CH_2)_nC(O)$— wherein n is 1 to 3;

B is $-N(R_4)CH(R_3)C(O)-$ wherein $R_4$ is hydrogen or loweralkyl and $R_3$ is loweralkyl, cycloalkyl or cycloalkylalkyl;

C is $-N(R_5)CH(R_6)C(O)-$ wherein $R_5$ is hydrogen or loweralkyl and $R_6$ is hydrogen, loweralkyl, cycloalkyl or cycloalkylalkyl;

R is loweralkyl, cycloalkyl, cycloalkylalkyl, aryl or bicyclic heterocyclic;

P4 is hydrogen, loweralkyl or benzyl;

X is $-CH_2-$ or $-C(O)-$;

D is

1) $-OR_7$ wherein $R_7$ is hydrogen, loweralkyl, cycloalkyl or cycloalkylalkyl;

2) $-NR_8R_9$ wherein $R_8$ and $R_9$ are independently selected from hydrogen, loweralkyl, cycloalkyl, cycloalkylalkyl and $-(CH_2)_m-Z$ wherein m is 2 to 8 and Z is $-OH$, heterocyclic, $-SO_3H$, $-CO_2R_{10}$ wherein $R_{10}$ is hydrogen or loweralkyl or Z is $-NR_{11}R_{12}$ wherein $R_{11}$ and $R_{12}$ are independently selected from hydrogen, loweralkyl, cycloalkyl and cycloalkylalkyl;

(3) $-NHCH\ (R_{13})C(O)-$ wherein $R_{13}$ is hydrogen, loweralkyl, cycloalkyl or cycloalkylalkyl; or (4) $-NHCH(R_{13})C(O)NHCH(R_{14})C(O)-$ wherein $R_{13}$ is hydrogen, loweralkyl, cycloalkyl or cycloalkylalkyl and $R_{14}$ is hydrogen, loweralkyl, cycloalkyl, cycloalkylalkyl, aminocarbonylalkyl, cyanoalkyl, carboxyalkyl or alkoxycarbonylalkyl; and E is (1) absent;

(2) $-OR_{15}$ wherein $R_{15}$ is hydrogen, loweralkyl, cycloalkyl or cycloalkylalkyl; or (3) $-NR_{16}R_{17}$ wherein $R_{16}$ and $R_{17}$ are independently selected from hydrogen, loweralkyl, cycloalkyl, cycloalkylalkyl and $-(CH_2)_p-Y$ wherein p is 2 to 8 and Y is $-OH$, heterocyclic, $-SO_3H$, $-CO_2R_{18}$ wherein $R_{18}$ is hydrogen or loweralkyl or Y is $-NR_{19}R_{20}$ wherein $R_{19}$ and $R_{20}$ are independently selected from hydrogen, loweralkyl, cycloalkyl and cycloalkylalkyl; or a pharmaceutically acceptable salt, ester or prodrug thereof.

In accordance with the present invention there are also endothelin converting enzyme inhibiting compounds of the formula (III):

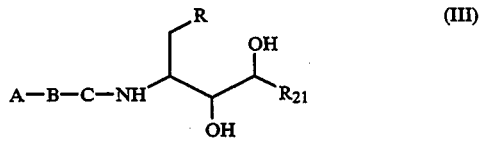

(III)

wherein

A is hydrogen, an N-protecting group, $R_1NHCH(R_2)C(O)-$ wherein $R_1$ is H or an N-protecting group and $R_2$ is hydrogen, loweralkyl, cycloalkyl, cycloalkylalkyl, carboxyalkyl, alkoxycarbonylalkyl or arylalkoxycarbonylalkyl; or A is $HO_2C(CH_2)_nC(O)-$ wherein n is 1 to 3; or A is $R_{1a}C\ (O)-$ or $R_{1a}S(O)_2-$ wherein $R_{1a}$ is heterocyclic; or A is (aminoalkyl)(alkyl)aminocarbonyl, (alkylaminoalkyl)(alkyl)aminocarbonyl, (dialkylaminoalkyl)(alkyl)aminocarbonyl, (aminoalkyl)(alkyl)aminosulfonyl, (alkylaminoalkyl)(alkyl)aminosulfonyl, (dialkylaminoalkyl)(alkyl)aminosulfonyl, (heterocyclicalkyl)(alkyl)aminocarbonyl or (heterocyclicalkyl)(alkyl)aminosulfonyl;

B is $-N(R_4)CH(R_3)C(O)-$ wherein $R_4$ is hydrogen or loweralkyl and $R_3$ is loweralkyl, cycloalkyl or cycloalkylalkyl;

C is $-N(R_5)CH(R_6)C(O)-$ wherein $R_5$ is hydrogen or loweralkyl and $R_6$ is loweralkyl, cycloalkyl or cycloalkylalkyl;

R is loweralkyl, cycloalkyl, cycloalkylalkyl, aryl or bicyclic heterocyclic; and $R_{21}$ is loweralkyl, cycloalkyl or cycloalkylalkyl; or a pharmaceutically acceptable salt, ester or prodrug thereof.

The chiral centers of the compounds of the invention can be racemic or asymmetric. Racemic mixtures, mixtures of diastereomers, as well as single diastereomers of the compounds of the invention are included in the present invention. The terms "S" and "R" configuration are as defined by the IUPAC 1974 Recommendations for Section E, Fundamental Stereochemistry, Pure Appl. Chem. (1976) 45, 13–30.

The terms "Ala", "Asn", "Asp", "Ile" and "Val" as used herein refer to alanine, asparagine, aspartic acid, isoleucine and valine, respectively. In general, the amino acid abbreviations used herein follow the IUPAC-IUB Joint Commission on Biochemical Nomenclature for amino acids and peptides (Eur. J. Biochem. 1984, 158, 9–31).

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. In particular, N-protecting groups include formyl, acetyl, benzoyl, pivaloyl, phenylsulfonyl, benzyl, t-butyloxycarbonyl (Boc), benzyloxycarbonyl (Cbz) and the like. N-protecting groups also include an L- or D-aminoacyl residue, which can itself be N-protected.

The term "O-protecting group" as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). O-protecting groups comprise substituted methyl ethers, for example, methoxymethyl, benzyloxymethyl, 2-methoxyethoxymethyl, 2-(trimethylsilyl) ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "aryl" as used herein refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide. In addition, substituted aryl groups include tetrafluorophenyl and pentafluorophenyl.

The term "arylalkyl" as used herein refers to an aryl group appended to a loweralkyl radical, for example, benzyl and the like.

The term "cycloalkyl" as used herein refers to an aliphatic ring having 3 to 7 carbon atoms including, but not limited to, cyclopropyl, cyclopentyl, cyclohexyl and the like. Cycloalkyl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a cycloalkyl group appended to a loweralkyl radical, including but not limited to cyclohexylmethyl.

The term "carboxyalkyl" as used herein refers to a loweralkyl radical to which is appended a carboxyl (—COOH) group.

The term "alkoxycarbonylalkyl" as used herein refers to a loweralkyl radical to which is appended an alkoxycarbonyl group (i.e., —C(O)OR$_{30}$ wherein R$_{30}$ is loweralkyl).

The term "arylalkoxycarbonylalkyl" as used herein refers to a loweralkyl radical to which is appended an arylalkoxycarbonyl group (i.e., —C(O)OR$_{50}$ wherein R$_{50}$ is an arylalkyl group).

The term "aminocarbonylalkyl" as used herein refers to a loweralkyl radical to which is appended —C(O)NH$_2$.

The term "cyanoalkyl" as used herein refers to a loweralkyl radical to which is appended a cyano group (—CN).

The term "alkylamino" as used herein refers to R$_{51}$NH— wherein R$_{51}$ is a loweralkyl group.

The term "dialkylamino" as used herein refers to R$_{52}$R$_{53}$N— wherein R$_{52}$ and R$_{53}$ are independently selected from loweralkyl.

The term "aminoalkyl" as used herein refers to a loweralkyl radical to which is appended an amino group (—NH$_2$).

The term "alkylaminoalkyl" as used herein refers to a loweralkyl radical to which is appended an alkylamino group.

The term "dialkylaminoalkyl" as used herein refers to a loweralkyl radical to which is appended a dialkylamino group.

The term "(aminoalkyl)(alkyl)aminocarbonyl" as used herein refers to R$_{54}$R$_{55}$NC(O)— wherein R$_{54}$ is an aminoalkyl group and R$_{55}$ is a loweralkyl group.

The term "(aminoalkyl)(alkyl)aminosulfonyl" as used herein refers to R$_{54}$R$_{55}$NS(O)$_2$— wherein R$_{54}$ is an aminoalkyl group and R$_{55}$ is a loweralkyl group.

The term "(alkylaminoalkyl)(alkyl)aminocarbonyl" as used herein refers to R$_{56}$R$_{57}$NC(O)— wherein R$_{56}$ is an alkylaminoalkyl group and R$_{57}$ is a loweralkyl group.

The term "(alkylaminoalkyl)(alkyl)aminosulfonyl" as used herein refers to R$_{56}$R$_{57}$NS(O)$_2$— wherein R$_{56}$ is an alkylaminoalkyl group and R$_{57}$ is a loweralkyl group.

The term "(dialkylaminoalkyl)(alkyl)aminocarbonyl" as used herein refers to R$_{58}$R$_{59}$NC(O)— wherein R$_{58}$ is a dialkylaminoalkyl group and R$_{59}$ is a loweralkyl group.

The term "(dialkylaminoalkyl)(alkyl)aminosulfonyl" as used herein refers to R$_{58}$R$_{59}$NS(O)$_2$— wherein R$_{58}$ is a dialkylaminoalkyl group and R$_{59}$ is a loweralkyl group.

The term "(heterocyclicalkyl)(alkyl)aminocarbonyl" as used herein refers to R$_{60}$R$_{61}$NC(O)— wherein R$_{60}$ is a heterocyclicalkyl group and R$_{61}$ is a loweralkyl group.

The term "(heterocyclicalkyl)(alkyl)aminosulfonyl" as used herein refers to R$_{60}$R$_{61}$NS(O)$_2$— wherein R$_{60}$ is a heterocyclicalkyl group and R$_{61}$ is a loweralkyl group.

The term "heterocyclic ring" or "heterocyclic" as used herein refers to any 3— or 4-membered ring containing a heteroatom selected from oxygen, nitrogen and sulfur; or a 5— or 6-membered ring containing one, two or three nitrogen atoms; one nitrogen and one sulfur atom; or one nitrogen and one oxygen atom. The 5-membered ring has 0–2 double bonds and the 6-membered ring has 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl or benzothienyl and the like). Heterocyclics include: azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Heterocyclics can be unsubstituted or monosubstituted or disubstituted with substituents independently selected from hydroxy, halo, oxo (=O), alkylimino (R*N= wherein R* is a loweralkyl group), amino, alkylamino, dialkylamino, alkoxy, polyalkoxy, haloalkyl, cycloalkyl, aryl, arylalkyl, —COOH, —SO$_3$H and loweralkyl. In addition, nitrogen containing heterocycles can be N-protected.

The term "heterocyclicalkyl" as used herein refers to heterocyclic group appended to a loweralkyl radical.

Representative compounds of the invention include: N-{(S)-2-[(tert-Butyloxycarbonyl)amino]-3,3-dimethylbutanoyl}-Isoleucyl-Statyl Ethyl ester; N-{(S)-2-[(tert-Butyloxycarbonyl)amino]-3,3-dimethylbutanoyl}-Isoleucyl-Statyl-OH; N-{(S)-2-[(tert-Butyloxycarbonyl)amino]-2-cyclohexylacetyl}-Isoleucyl-Statyl Ethyl ester; N-{(S)-2-[(tert-Butyloxycarbonyl)amino]-2-cyclohexylacetyl}-Isoleucyl-Statyl-OH; N-Boc-Isoleucyl-Isoleucyl-Statyl Carboxamide; N-Boc-Isoleucyl-Isoleucyl-Statyl (4-Hydroxybutyl)carboxamide; N-Boc-Isoleucyl-Isoleucyl-Statyl (5-Hydroxyamyl)carboxamide; N-Boc-Isoleucyl-Isoleucyl-Statyl (6-Hydroxyhexyl)carboxamide; [1-[(N-Cbz-Isoleucyl-Isoleucyl)Amino]-3-methybutyl(methoxy)phosphinyl]acetic acid tert-Butyl ester; N-Boc-Isoleucyl-Isoleucyl-Statyl-OH; N-Succinyl-Isoleucyl-Isoleucyl-Statyl-Valyl-OH; N-

Boc-Cyclohexylalanyl-Isoleucyl-Statyl Ethyl ester; N-Boc-Isoleucyl-Isoleucyl-Statyl-β-Alanyl Ethyl ester; N-Boc-Isoleucyl-Isoleucyl-Statyl Isobutylcarboxamide; N-Boc-Cyclohexylalanyl-Isoleucyl-Statyl-OH; N-Boc-Isoleucyl-Isoleucyl-Statyl-β-Alanyl-OH; N-Boc-Isoleucyl-Isoleucyl-Tryptophanyl Carboxaldehyde; (4S)-4-(N-Boc-Isoleucyl-Isoleucyl-Amino)-5-(3-indolyl)-3-hydroxypentanoic acid; (4S)-4-(N-Succinyl-Isoleucyl-Isoleucyl-Amino)-5-(3-indolyl)-3-hydroxypentanoic acid Ethyl ester; N-[(4S)-4-(N-Boc-Isoleucyl-Isoleucyl-Amino)-5-(3-indolyl)-3-hydroxypentanoyl]-Valyl-OH; N-[(4S)-4-(N-Boc-Aspartyl-Isoleucyl-Isoleucyl-Amino)-5-(3-indolyl) -3-hydroxypentanoyl]-Valyl-OH; (4S)-4-(N-Boc-Cyclohexylalanyl-Isoleucyl-Amino)-5-(3-indolyl) -3-hydroxypentanoic acid; N-[(4S)-4-(N-Boc-Cyclohexylalanyl-Isoleucyl-Amino)-5-(3-indolyl) -3-hydroxypentanoyl]-Valyl-OH; (2S,3R,4S)-2-(N-Boc-Isoleucyl-Isoleucyl-Amino)-1-cyclohexyl -3,4-dihydroxy-6-methylheptane; (2S,3R,4S)-2-(N-Succinyl-Isoleucyl-Isoleucyl-Amino)-1-cyclohexyl -3,4-dihydroxy-6-methylheptane; (2S,3R,4S)-2-(N-Boc-Aspartyl (β-O-Benzyl)-Isoleucyl-Isoleucyl-Amino) -1-cyclohexyl-3,4-dihydroxy-6-methylheptane; (2S,3R,4S)-2-(N-Acetyl-Isoleucyl-Isoleucyl-Amino)-1-cyclohexyl -3,4 -dihydroxy-6-methylheptane; (2S,3R,4S)-2-(N-Boc-Cyclohexylalanyl-Isoleucyl-Amino)-1-cyclohexyl -3,4-dihydroxy-6-methylheptane; (2S,3R,4S)-2-(N-Boc-Isoleucyl-Isoleucyl-Amino)-1-(2-naphthyl) -3,4-dihydroxy-6-methylheptane; (2S,3R,4S)-2-(N-Boc-Cyclohexylalanyl-Isoleucyl-Amino)-1-(2-naphthyl) -3,4-dihydroxy-6-methylheptane; (2S,3R,4S)-2-(N-Boc-Cyclohexylalanyl-Isoleucyl-Amino)-1-(1 -naphthyl) -3,4 -dihydroxy-6-methylheptane; N-Boc-Isoleucyl-Isoleucyl-Statyl Isopropylcarboxamide; [1-[N-Cbz-Isoleucyl-Isoleucyl-Amino]-3-methylbutyl (hydroxy)-phosphinyl]acetic acid tert-Butyl ester; N-Boc-Isoleucyl-Isoleucyl-Statyl Isoamylcarboxamide; N-Boc-Isoleucyl-Isoleucyl-Statyl Cyclohexylmethylcarboxamide; [1-[N-(N-Cbz-[(S)-2-Amino-3,3-dimethyl-butanoyl])-Isoleucyl-Amino]-3-methylbutyl(hydroxy)-phosphinyl]acetic acid tert-Butyl ester; [1-[N-Cbz-Isoleucyl-Isoleucyl-Amino]-3-methylbutyl (hydroxy)-phosphinyl]acetyl Isobutylcarboxamide; (2S,3R,4S)-2-(N-Boc-Cyclohexylalanyl-Isoleucyl-Amino)-1-(3-indolyl) -3,4 -dihydroxy-6-methylheptane; N-Boc-Cyclohexylalanyl-Isoleucyl-Statyl Isobutylcarboxamide; N-Boc-Cyclohexylalanyl-Isoleucyl-Statyl N-(2-(2-Pyridyl)ethyl)Carboxamide; N-Boc-Cyclohexylalanyl-Isoleucyl-Statyl N-(2-N',N'-Dimethylaminoethyl) Carboxamide; N-Boc-Cyclohexylalanyl-Isoleucyl-Statyl N-(2-(Morpholin-4-yl)ethyl)Carboxamide; (2S,3R,4S)-2-{[N-(4-Methylpiperazin-1-yl-carbonyl)-Cyclohexylalanyl-Isoleucyl]amino}-1-(2-naphthyl)-3,4-dihydroxy-6-methylheptane Hydrochloride; N-Boc-tert-Butylalanyl-Isoleucyl-Statyl-OEt; N-Boc-tert-Butylalanyl-Isoleucyl-Statyl-OH; (2S,3R,4S)-2-{[N-Boc-Aspartyl(β-O-Benzyl)-Isoleucyl-Isoleucyl-amino}-1-(2-naphthyl)-3,4-dihydroxy-6methylheptane; N-Boc-Isoleucyl-Isoleucyl-Statyl N-(2-(2-Pyridyl)ethyl)Carboxamide; (2S,3R,4S)-2-{[N-Succinyl-Cyclohexylalanyl-Isoleucyl]amino}-1-(2 -naphthyl)-3,4 -dihydroxy-6methylheptane; (2S,3R,4S)-2-{[N-Boc-Cyclohexylalanyl-Isoleucyl]amino}-1-(4-tert-butylphenyl) -3,4 -dihydroxy-6-methylheptane; (2S,3R,4S)-2-{[N-Acetyl-Cyclohexylalanyl-Isoleucyl]amino}-1-(4 -tert-butylphenyl)-3,4-dihydroxy-6-methylheptane; (2S,3R,4S)-2-{[N-Acetyl-Cyclohexylalanyl-Isoleucyl-]amino}-1 -(2 -naphthyl) -3,4 -dihydroxy-6-methylheptane; N-Boc-Isoleucyl-Isoleucyl-Statyl N-Methyl-N-IsobutylCarboxamide; (2S,3R,4S)-2-{[N-(Morpholin-1-yl-carbonyl)-Cyclohexylalanyl-Isoleucyl]amino}-1-(2-naphthyl)-3,4-dihydroxy-6 -methylheptane; (2S,3R,4S)-2-{[{N-(N,N-Dimethylaminoethyl)-N-methylamino}carbonyl-Cyclohexylalanyl-Isoleucyl-]amino}-1-(2-naphthyl) -3,4-dihydroxy-6-methylheptane; and (2S,3R,4S)-2-{[N-(4-Methylpiperazin-1-yl-sulfonyl)-Cyclohexylalanyl-Isoleucyl]amino}-1-(2-naphthyl)-3,4-dihydroxy-6-methylheptane.

The compounds of the invention can be prepared as shown in Schemes I-VII. Throughout the schemes, substituents A, B, C, D, E, X, R, $R_1$, $R_2$, etc., are as defined herein-above.

The general synthetic approach is depicted in Scheme I. The free amine or hydrochloride salt (which has been converted to its free base in situ) of the C-terminal residue 1 is coupled with the appropriately N-protected amino acid 2 through its carboxylic acid moiety using standard peptide coupling methods. The N-protecting group on the coupled product 3 is removed, and the residue is converted to its free base either in a separate step or in situ. The deprotected residue is then coupled to the carboxylic acid of an appropriately N-protected amino acid 4 using standard peptide coupling methods. Finally, peptide 5 can be converted to I (A is hydrogen, $R_1NHCH(R_2)C(O)-$ or $HO_2C(CH_2)_n-C(O)-$) by removal of the protecting group, optionally followed by coupling of the $R_1NHCH(R_2)C(O)-$ or $HO_2C(CH_2)_nC(O)-$ group.

Alternatively, the process can begin at the the N-terminal end of the molecule. Thus, the carboxylic acid moiety of N-protected amino acid 6 (wherein A is an N-protecting group or $R_1NHCH(R_2)C(O)-$) is coupled with 2 to provide peptide 7 ($R_{40}$ is loweralkyl or benzyl). The ester 7 is converted to the carboxylic acid by hydrolysis or catalytic hydrogenation. The carboxylic acid derived from 7 is then coupled to 1 to provide I. In this alternative method when A is $HO_2C(CH_2)_nC(O)-$, this substitutent (i.e., A) is introduced during the last step of the sequence.

The synthesis of statine and statine derivatives 1 is illustrated in Scheme II. The appropriate N-protected amino acid 8 is converted to its 3,5-dimethylpyrazolide using 3,5-dimethypyrazole and 1-hydroxybenzotriazole and 1-(dimethylamino-propyl)-3-ethylcarbodiimide or other appropriate coupling conditions and catalysts. The resultant pyrazolide 9 is reduced with lithium aluminum hydride or other appropriate reducing agent to give the amino acid carboxaldehyde 10. The enol ether of an alkyl acetate (such as ethyl acetate), prepared using lithium hexamethyldisilazide or other appropriate base, is reacted with the aldehyde to give the β-hydroxy ester 11. Hydroxy ester 11 can be further elaborated to provide 1.

Compounds 1 wherein X is $CH_2$ are obtained via the acid derived from ester 11. Hydrolysis of 11 provides the free acid which is converted to the 3,5-dimethyl-pyrazolide 11a as previously described. Reduction using lithium aluminum hydride or similar reducing agent provides the aldehyde 11b. The aldehyde is reductively aminated with $R_8NH-E$ to provide 11c, which can be further elaborated to provide 1.

The synthesis of the phosphorus derivatives of statine or statine derivatives 14 is shown in Scheme III. Derivatives of [(benzyloxycarbonyl)amino-1-substituted(methoxy)-phosphinyl]acetic acid ester 12 ($P_4$ is loweralkyl, $R_{41}$ is loweralkyl) can be prepared as described in the literature: Bartlett, P. A.; Kezer, W. B.; J. Am. Chem. Soc., 106, 4282 (1984). N-deprotection and dealkylation of the phosphinic acid (for example, using potassium cyanide and 1,4,7,10,13,16-hexaoxacyclooctadecane in dimethyl sulfoxide) provides 13. Compound 12 can also be elaborated to derivative 14, which can then be elaborated to the compounds of the invention II using the general methods outlined in Scheme I.

Scheme IV illustrates the synthesis of 2-amino-1-substituted-3,4-dihydroxy-alkanes 19 and is based on a literature procedure (Luly, J. R.; Hsiao, C. N.; BaMaung, N.; Plattner, J. J.; J. Org. Chem. 53, 6109 (1988)). The amino acid 8 is N-protected using di-tert-butyldicarbonate or some other N-protecting group to give 15. The carboxylic acid 15 is reduced using boranetetrahydrofuran complex or other appropriate reducing agent to give the alcohol 16. Using appropriate oxidizing conditions such as oxalyl chloride/dimethyl sulfoxide/methylene chloride, followed by triethylamine, the intermediate aldehyde is obtained. Trimethylsilyl cyanide and zinc iodide treatment yields the trimethylsilyl cyanohydrin, which upon reaction with a Grignard reagent $R_{21}MgCl$ (such as isobutylmagnesium chloride) affords the hydroxy ketone 17. Reduction using sodium borohydride or other appropriate reducing agent provides the diol 18. Removal of the N-protecting group provides the amino-diol 1, which can be elaborated to the compounds of the invention III using the general methods outlined in Scheme I.

Scheme V illustrates an alternative synthesis of 18. Reduction of ester 25 ($R^*$ is loweralkyl and the like), for example, with sodium borohydride, provides 16. Oxidation (for example, Swern oxidation), followed by reaction with the appropriate Wittig reagent (for example, $Ph_3P^+CH_2R_{21}$ $Br^-$/KOtBu in dimethyformamide or $Ph_3P^+CH_2R_{21}$ $Br^-$/potassium hexamethydisilazide in tetrahydrofuran) provides olefin 26. Oxidation (for example, $OsO_4$/N-methylmorpholine N-oxide), followed by purification (for example, recrystallization), gives 18.

Scheme VI illustrates an alternative preparation of 19 wherein $R_{21}$ is isobutyl. D-Isoascorbic acid 27 can be converted to the known lactol 29 (J.Am. Chem. Soc. 105 3661 (1983)). Reaction with $Ph_3P=CH(CH_3)_2$ provides 30. Oxidation to aldehyde 31, followed sequentially by reaction with benzylamine and a Grignard reagent (i.e., $RCH_2MgBr/CeCl_3$) gives amine 32. Deprotection of the amino group, reduction of the olefin and removal of the acetonide protecting group provides 19 wherein $R_{21}$ is isobutyl.

An alternative preparation of the reduced form of compound 31 (i.e., 33) is shown in Scheme VII. Epoxyalcohol 34 (J.Am. Chem. Soc. 109 1525 (1987)) is protected and then reacted with isopropyl Grignard to give 35. Reaction with camphorsulfonic acid (CSA), followed by ozonolysis, gives the aldehyde 33. Compound 33 can be converted to 19 by adapting the procedure outlined in Scheme VI.

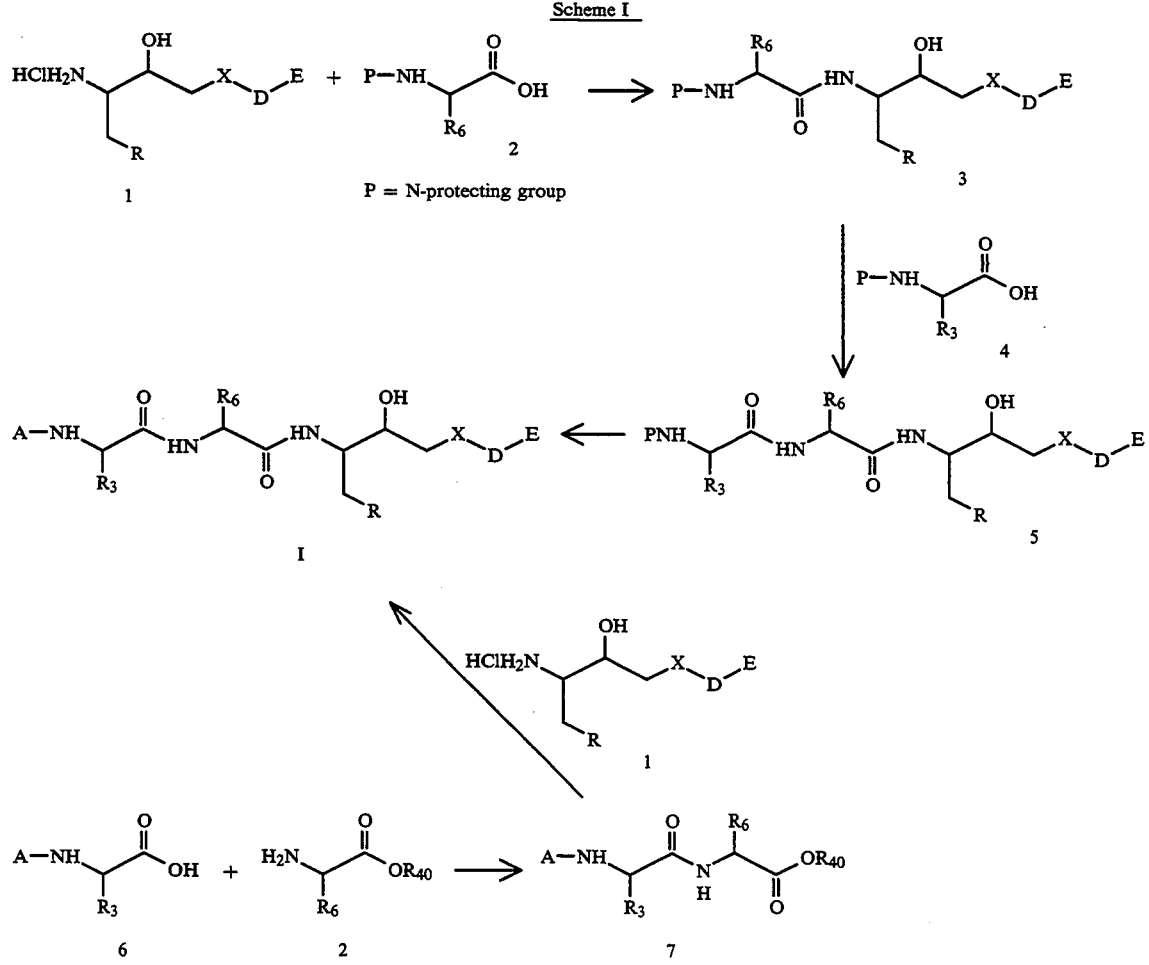

Scheme I

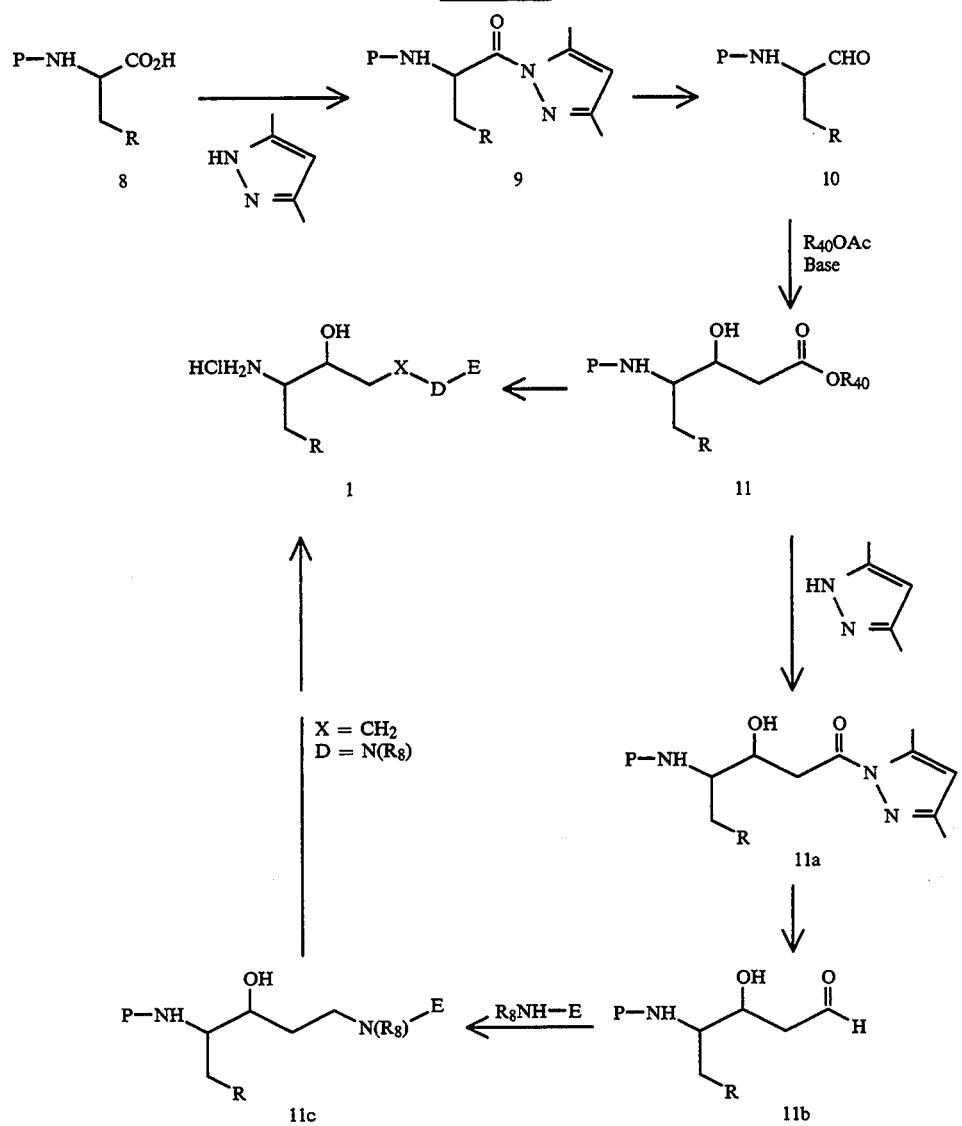
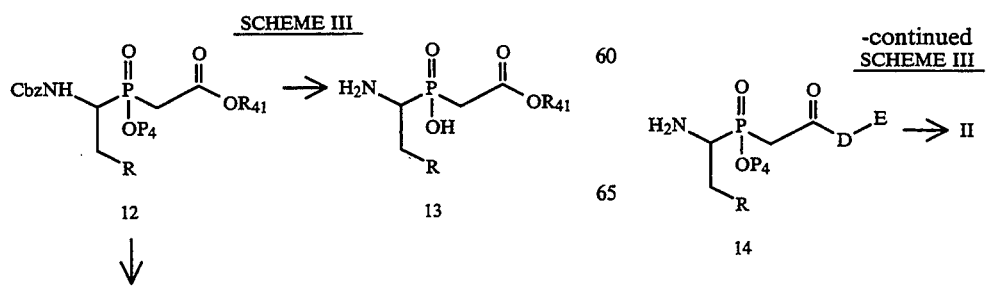

SCHEME IV
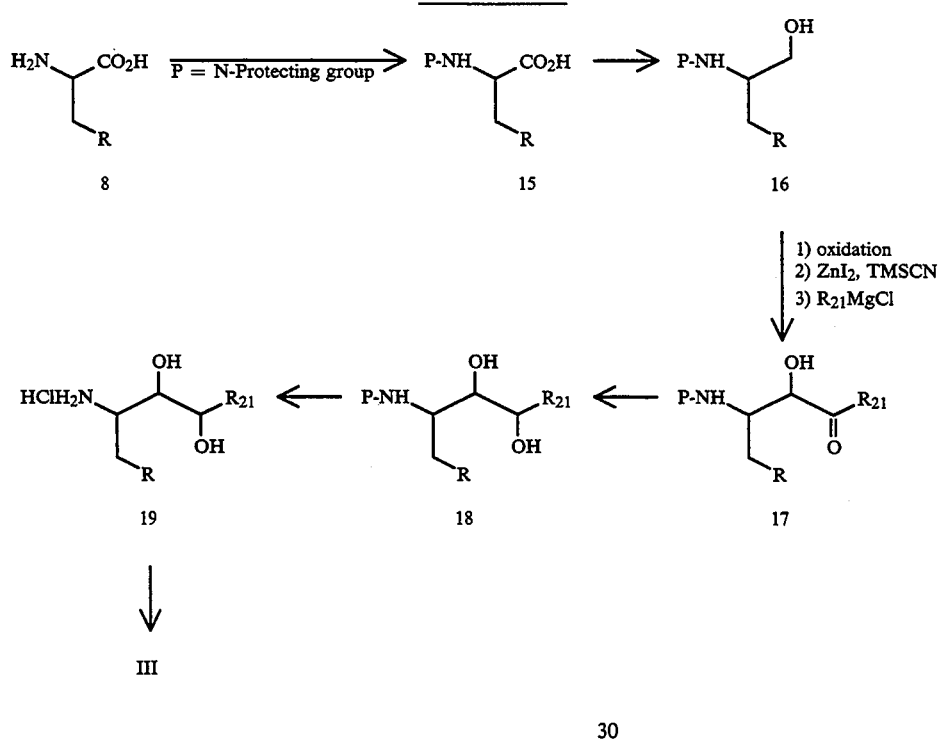
SCHEME V
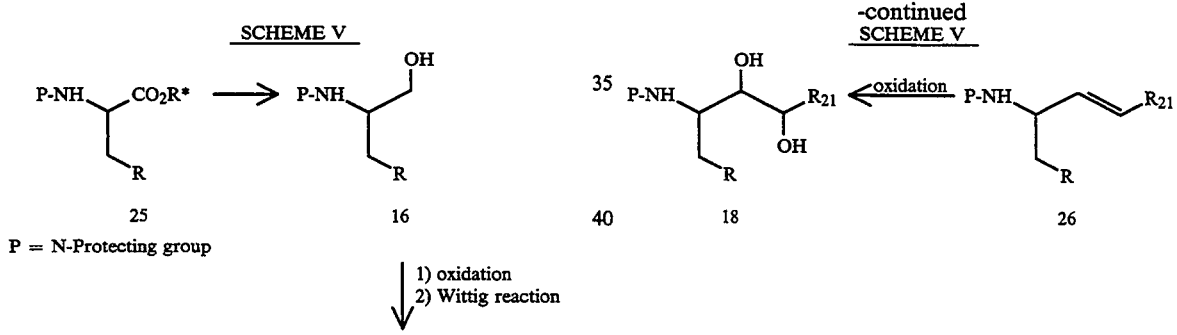
Scheme VI
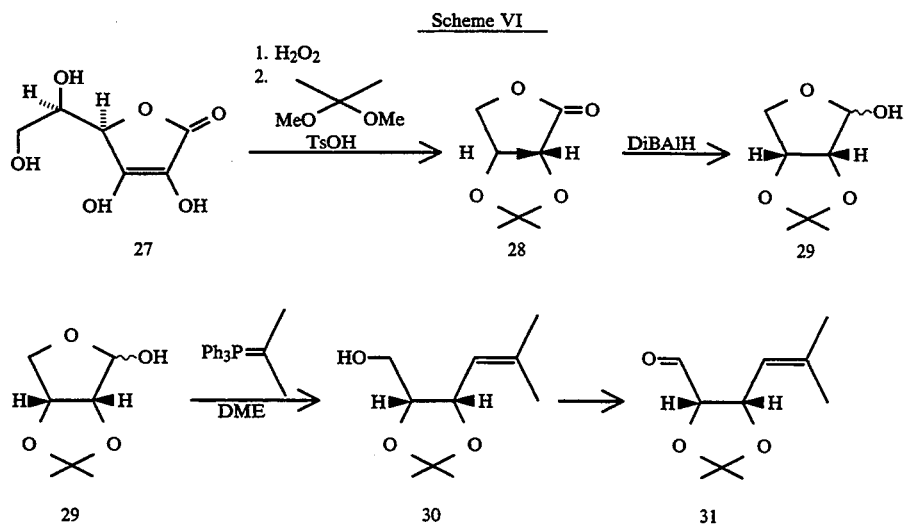

Scheme VI

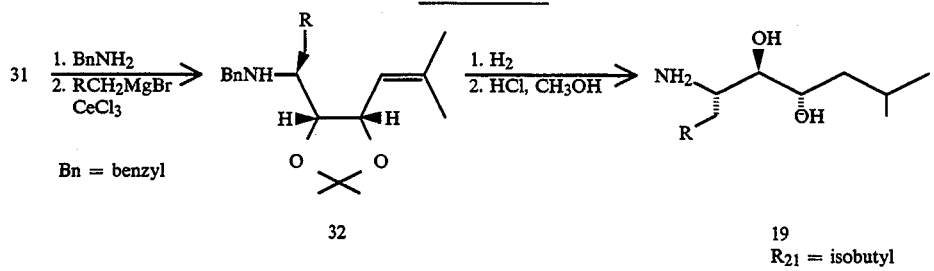

Scheme VII

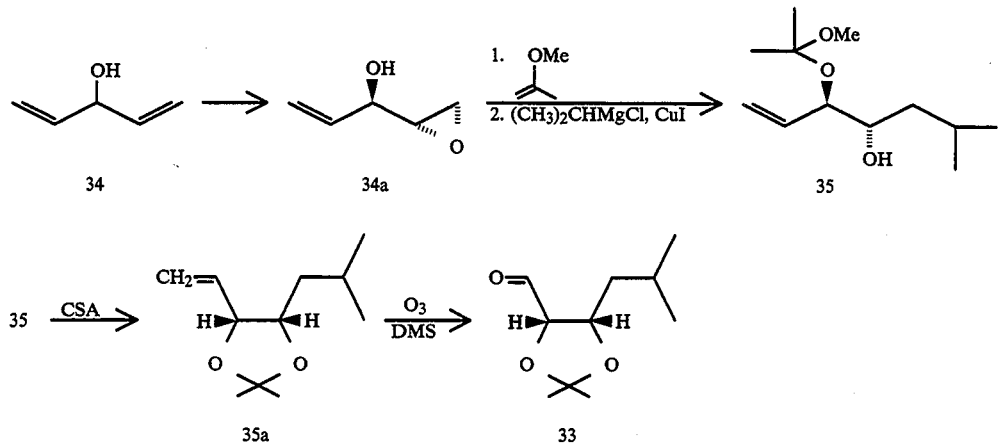

Compounds useful as intermediates for the preparation of compounds of the formula (I) include compounds of the formula:

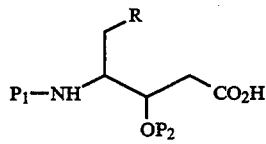

Fi wherein $P_1$ is hydrogen or an N-protecting group; $P_2$ is hydrogen or an O-protecting group; and R is loweralkyl, cycloalkyl, cycloalkylalkyl, aryl or bicyclic heterocyclic; or an ester, acid halide or activated ester derivative thereof.

Compounds useful as intermediates for the preparation of compounds of the formula (II) include compounds of the formula:

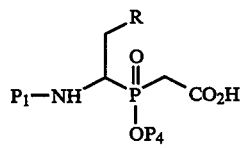

wherein $P_1$ is hydrogen or an N-protecting group; $P_4$ is hydrogen, loweralkyl or benzyl; and R is loweralkyl, cycloalkyl, cycloalkylalkyl, aryl or bicyclic heterocyclic; or an ester, acid halide or activated ester derivative thereof.

Compounds useful as intermediates for the preparation of compounds of the formula (III) include compounds of the formula:

wherein $P_1$ is hydrogen or an N-protecting group; R is loweralkyl, cycloalkyl, cycloalkylalkyl, aryl or bicyclic heterocyclic; $P_2$ and $P_3$ are independently selected from hydrogen and an O-protecting group; and $R_{21}$ is loweralkyl, cycloalkyl or cycloalkylalkyl; or a salt thereof.

The following examples will serve to further illustrate the preparation of the compounds of the invention.

EXAMPLE 1

N-{(S)-2-[(tert-Butyloxycarbonyl]amino]-3,3-dimethylbutanoyl}-Isoleucyl-Statyl Ethyl ester

EXAMPLE 1A

Boc-Leucyl-[3,5-dimethylpyrazolide]

To Boc-Leu-OH monohydrate (25 g, 0.10 mol), 3,5-dimethyl pyrazole (DMP) (11.6 g, 0.12 mol), and 1-hydroxybenzotriazole hydrate (HOBT) (16.2 g, 0.12 mol) combined in methylene chloride ($CH_2Cl_2$) (550 mL) and cooled to 2° C. was added 1-(3-dimethylaminopropyl)-3-ethylcarbodiimide hydrochloride (EDCI) (21.4 g, 0.11 mol). The reaction mixture was allowed to warm to room temperature, stirred overnight, and concentrated under reduced pressure. The residue was diluted with ethyl acetate (EtOAc) and washed with 1N $H_3PO_4$. The aqueous washes were back extracted with EtOAc and the combined EtOAc extracts were washed with 1N $H_3PO_4$ (2×), saturated $NaHCO_3$ (3×), and brine, dried (Na₂SO₄), and concentrated in vacuo to afford the title compound as a white solid. The 300 MHz ¹H NMR spectrum was found to be consistent with the proposed structure.

MS (DCI/NH₃) m/e 310 (M+H)⁺.

EXAMPLE 1B

Boc-Leucinal

To the product of Example 1a (25 g, 81 mmol) dissolved in anhydrous tetrahydrofuran (THF) (350 mL) and cooled to −78° C. was added lithium aluminum hydride (LAH) (5 g, 132 mmol) in 5 portions over 70 minutes. Following the addition, the reaction mixture was maintained at −78° C. for an additional 60 minutes and then carefully poured with vigorous stirring into 10% citric acid (1200 mL). This mixture was extracted with diethyl ether (Et2O) (3×500 mL) and the combined organic extracts were washed with brine, dried (MgSO₄), and concentrated in vacuo to give a tacky residue. The 300 MHz ¹H NMR spectrum was found to be consistent with the proposed structure. MS (DCI/NH₃) m/e 216 (M+H)⁺.

EXAMPLE 1C

Boc-Statyl Ethyl ester

Ethyl acetate, which had been dried by refluxing overnight over CaH₂ and distilled, (14 mL, 0.143 mol) was added to freshly distilled THF (450 mL) and cooled to −78° C. A 1M solution of lithium hexamethyldisilazide (LHMDS) (120 mL) was added over 30 minutes under a N₂ atmosphere. After one hour at −78° C., the product of Example 1b (8.5 g, 0.039 mol) in freshly distilled THF (50 mL) was added, and the reaction mixture was stirred at −78° C. for 70 minutes and then quenched by addition to 1N HCl (700 mL). This mixture was extracted with Et₂O (2×400 mL) and the organic extracts washed with saturated NaHCO₃ solution (2×), brine, dried (MgSO₄), and concentrated in vacuo to afford 11.6 g of an orange oil. Flash chromatography on silica gel (350 g) eluting with 15% EtOAc in hexanes afforded 4.9 g of the title compound.

MS (DCI/NH₃) m/e 304 (M+H)⁺. The 300 MHz ¹H NMR spectrum was found to be consistent with the proposed structure.

EXAMPLE 1D

Statyl Ethyl ester HCl salt

The product of Example 1c (203 mg, 0.67 mmol) dissolved in 4N HCl in dioxane (3 mL) was stirred at room temperature for 1 hour and then concentrated in vacuo to give the title product as an oil. MS (DCI/NH₃) m/e 204 (M+H)⁺ of the free base. The 300 MHz ¹H NMR spectrum was found to be consistent with the proposed structure.

EXAMPLE 1E

N-Boc-Isoleucyl-Statyl Ethyl ester

To the product of Example 1d (152 mg, 0.63 mmol) dissolved in CH₂Cl₂ (3 mL) was added N-methylmorpholine (NMM) (0.07 g, 0.70 mmol) and the reaction mixture cooled to 0° C. Boc-Ile-OH hemihydrate (152 mg, 0.63 mmol) was added followed by 1-hydroxybenzotriazole (HOBT) and EDCI (134 mg, 0.70 mmol). The reaction mixture was stirred at 0° C. and allowed to warm to room temperature overnight. The reaction mixture was diluted with EtOAc, washed with 1N H₃PO₄ (3×), saturated NaHCO₃ (3×), and brine, dried (Na₂SO₄), and concentrated in vacuo to give a solid. Recrystallization from hexane afforded the title compound as a white crystalline solid in 73% yield. The 300 MHz ¹H NMR spectrum was found to be consistent with the proposed structure. MS (DCI/NH₃) m/e 417 (M+H)⁺, 434 (M+H+NH₃)⁺.

EXAMPLE 1F

Isoleucyl-Statyl Ethyl ester HCl salt

The product of Example 1e (200 mg, 0.48 mmol) was deprotected as described in Example 1d to afford an oil which was dissolved in H₂O (15 mL) and lyophilized to give the title compound as a white amorphous solid (169 mg, 100%).

The 300 MHz ¹H NMR spectrum was found to be consistent with the proposed structure.

MS (FAB+) m/e 304 (M+H)⁺.

EXAMPLE 1G (S)-2-[(tert-Butyloxycarbonyl)amino]-3,3-dimethylbutanoic acid

To L-t-Butylglycine (1.00 g, 7.6 mmol) dissolved in 1N NaOH (9.5 mL) and THF (8 mL) was added di-t-butyldicarbonate (1.67 g, 7.6 mmol) in THF (1.5 mL). The reaction mixture was stirred overnight at room temperature and extracted with hexanes (3×). The combined organic extracts were washed with saturated NaHCO₃ (2×). The combined aqueous layers were adjusted to pH 2 with 1.1N NaHSO₄ and back-extracted with Et₂O (3×). The combined organic extracts were washed with brine, dried (Na₂SO₄), and concentrated in vacuo to give the title compound as an oil (1.70 g) which solidified on standing.

MS (DCI/NH₃) m/e 232 (M+H)⁺, 249 (M+H+NH₃)⁺.

The 300 MHz ¹H NMR spectrum was found to be consistent with the proposed structure.

EXAMPLE 1H

N-{(S)-2-[(tert-Butyloxycarbonyl)amino]-3,3-dimethylbutanoyl}-Isoleucyl-Statyl Ethyl ester The product of Example 1f (95 mg, 0.27 mmol) was partitioned between EtOAc (20 mL) and saturated NaHCO₃ solution (30 mL). The aqueous phase was extracted with additional EtOAc (2×10 mL) and the combined organic extracts were washed with brine, dried (Na₂SO₄), and concentrated in vacuo to afford the free base (80 mg, 94%) as a white powder.

To the free base dissolved in CH₂Cl₂ (8 mL) and cooled to 0° C. was added Example 1g (58 mg, 0.25 mmol) followed by HOBT (41 mg, 0.3 mmol) and EDCI (53 mg, 0.28 mmol). The reaction mixture was allowed to warm to room temperature overnight. EtOAc was added and the mixture washed with 1N H₃PO₄ (3×), saturated NaHCO₃ (3×), and brine (2×), dried (Na₂SO₄), and concentrated in vacuo to give a glassy residue which was crystallized from hot hexane to afford the title compound (120 mg, 91%) as an off-white solid. ¹H NMR (CDCl₃, 300 MHz) δ 0.8–1.0 (m, 12H), 1.00 (s, 9H), 1.05–1.95 (m, 9H), 1.44 (s, 9H), 2.48 (d, 2H), 3.4 (bd, 1H), 3.75–4.3 (m, 6H), 5.18 (m, 1H), 6.25 (m, 2H). Anal calcd for C₂₇H₅₁N₃O₇: C, 61.22; H, 9.70; N, 7.93;

Found: C 60.94, H 9.78, N 8.14.

MS(FAB+) m/e 530 (M+H)+.

EXAMPLE 2

N-{(S)-2-[(tert-Butyloxycarbonyl)amino]3,3-dimethyl-butanoyl}-Isoleucyl-Statyl-OH The product of Example 1h (46 mg, 0.087 mmol) in MeOH (2.5 mL) was treated with 2N NaOH (0.1 mL) and stirred at room temperature for 3.5 hours. An additional aliquot of 2N NaOH (0.1 mL) was added and stirring continued for an additional 2.5 hours. The reaction mixture was concentrated in vacuo, dissolved in H$_2$O, and acidified to pH 1 with 1M H$_3$PO$_4$. The product was extracted with EtOAc, washed with H$_2$O (2×), brine, dried (Na$_2$SO$_4$), and concentrated in vacuo to afford a white solid (44 mg). $^1$H NMR (CDCl$_3$, 300 MHz) δ 0.83–1.03 (m, 12H), 1.00 (s, 9H), 1.03–1.66 (m, 5H), 1.44 (s, 9H), 1.95 (bs, 1H), 2.56 (bt, 2H), 3.7–4.3 (m, 4H), 5.16 (m, 1H), 6.75 (m, 2H).

Anal calcd for C$_{25}$H$_{47}$N$_3$O$_7$ 0.5 H$_2$O: C, 58.80; H, 9.47; N, 8.23; Found: C, 58.63; H, 9.32; N. 8.20.

MS (FAB+) m/e 502 (M+H)+, 519 (M+H+NH$_3$)+.

EXAMPLE 3

N-{(S)-2-[(tert-Butyloxycarbonyl)amino]-2-cyclohexylacetyl}-Isoleucyl-Statyl Ethyl ester

EXAMPLE 3A (S)-2-Amino-2-cyclohexylacetic acid

L-Phenylglycine (8.04 g, 53 mmol) was reduced by catalytic hydrogenation using PtO$_2$ in 80% acetic acid (HOAc) (200 mL). The catalyst was removed by filtration and the HOAc removed under reduced pressure to afford the title compound as a white solid (7.8 g, 94%). The 300 MHz $^1$H NMR spectrum was found to be consistent with the proposed structure.

MS (FAB) m/e 158 (M+H)+.

EXAMPLE 3B (S )-2-[(tert-Butyloxycarbonyl)amino]-2-cyclohexylacetic acid

To the product of Example 3a (974 mg, 6.2 mmol) dissolved in 1N NaOH (8 mL) was added THF (7 mL) followed by di-t-butyl-dicarbonate (1.34 g, 6.2 mmol) in THF (2 mL). The reaction was stirred overnight at room temperature and then 2N NaOH (2 mL) was added. The reaction mixture was extracted with hexanes (3×) and the combined organic extracts were washed with saturated NaHCO$_3$ solution (2×). The combined aqueous layers were acidified to pH 2 with 1.1M NaHSO$_4$ and extracted with Et$_2$O (2×). The ether extracts were dried (Na$_2$SO$_4$) and concentrated in vacuo to give the title compound (1.37 g, 86%). The 300 MHz $^1$H NMR spectrum was found to be consistent with the proposed structure.

MS (DCI/NH$_3$) m/e 275 (M+H+NH$_3$)+.

EXAMPLE 3C

N-{(S)-2-[{tert-Butyloxycarbonyl)amino]-2-Cyclohexylacetyl}-Isoleucyl-Statyl Ethyl ester To the product of Example 1f (47 mg, 0.15 mmol) dissolved in CH$_2$Cl$_2$ (5 mL) and cooled to 0° C. was added the product of Example 3b (38 mg, 0.15 mmol) followed by HOBT (24 mg, 0.18 mmol) and EDCI (31 mg, 0.16 mmol). The reaction mixture was allowed to warm to room temperature overnight. The reaction mixture was diluted with EtOAc, washed with 1M H$_3$PO$_4$ (3×), saturated NaHCO$_3$ (3×), and brine, dried (Na$_2$SO$_4$), and concentrated in vacuo to give a white solid (62 mg), which was recrystallized from EtOAc/hexanes. $^1$H NMR (CDCl$_3$, 300 MHz) δ 0.9 (m, 12H), 1.0–2.15 (m, 20H), 1.45 (s, 9H), 2.5 (bd, 2H), 3.3–3.5 (d of d, 1H), 3.8–4.3 (m, 6H), 5.0 (bt, 1H), 6.4 (m, 2H).

Anal calcd for C$_{29}$H$_{53}$N$_3$O$_7$: C, 62.67; H, 9.61; N, 7.56;

Found: C, 62.41; H, 9.54; N, 7.51.

MS (FAB) m/e 556 (M+H) +.

EXAMPLE 4

N-{(S)-2-[(tert-Butyloxycarbonyl)amino]-2-cyclohexylacetyl}-Isoleucyl-Statyl-OH The product of Example 3c was hydrolyzed in analogy to Example 2 to give a solid which was recrystallized from CH$_2$Cl$_2$/hexane to give the title compound (24 mg, 81%). NMR (CDCl$_3$, 300 MHz) δ 0.85–1.00 (m, 12H), 1.45 (s, 9H), 1.00–2.05 (m, 17H), 2.55 (bt, 2H), 3.80–4.30 (m, 4H), 5.10 (m, 1H), 6.7–6.95 (m, 2H). Anal calcd for C$_{27}$H$_{49}$N$_3$O$_7$ H$_2$O: C, 59.43; H, 9.42; N, 7.70; Found: C, 59.51; H, 9.13; N, 7.67.

MS (FAB) m/e 528 (M+H)+.

EXAMPLE 5

N-Boc-isoleucyl-Isoleucyl-Statyl Carboxamide

EXAMPLE 5A

N-Boc-Isoleucyl-Isoleucyl-Statyl Ethyl ester

Coupling of the product of Example 1f (200 mg, 0.63 mmol) with Boc-Ile-OH hemihydrate (152 mg, 0.63 mmol) by the method described in Example 1e afforded crude material which was recrystallized from EtOAc/hexane to give the title compound as a white crystalline solid (280 mg, 84%). The 300 MHz $^1$H NMR spectrum was found to be consistent with the proposed structure.

MS (FAB) m/e 530 (M+H)+.

EXAMPLE 5B

N-Boc-Isoleucyl-Isoleucyl-Statyl-OH

The product of Example 5a (274 mg, 0.52 mmol) was hydrolyzed by the method described in Example 2 to give the title compound as a white solid (240 mg, 93%). The 300 MHz $^1$H NMR spectrum was found to be consistent with the proposed structure.

MS (FAB) m/e 502 (M+H)+.

EXAMPLE 5C

N-Boc-Isoleucyl-Isoleucyl-Statyl Carboxamide

To the product of Example 5b (40 mg, 0.08 mmol) dissolved in THF (4 mL) and cooled to −5° C. was added N-methylmorpholine (NMM) (9 μL, 84 μmol) followed by isobutyl chloroformate (IBCF) (11μL, 84 μmol). The reaction mixture was stirred for 20 minutes and concentrated NH$_4$OH (25 μL, 0.36 mmol) was added. After 2.5 hours, the solvent was removed under reduced pressure, the residue was dissolved in MeOH and diluted with CHCl$_3$ and washed with 1M H$_3$PO$_4$ (2×), saturated NaHCO$_3$ (2×), and brine. Drying (Na$_2$SO$_4$) and concentration in vacuo followed by flash chromatography eluting with 93.5/6.5 CHCl$_3$/EtOH afforded the title compound (7 mg, 18%) as a white solid. $^1$H NMR (DMSO-D$_6$, 300 MHz) δ 0.8 (m, 18H), 1.4 (s, 9H), 1.0–1.8 (m, 9H), 2.0–2.2 (m, 2H), 3.6–3.9 (m, 3H), 4.35 (d of d, 1H), 6.8–7.7 (m, 4H). Anal calcd for $C_{25}H_{48}N_4O_6$: C, 59.97; H, 9.66; N, 11.19; Found: C, 59.77; H, 9.46; N, 10.77.

MS (FAB) m/e 501 (M+H)+.

EXAMPLE 6

N-Boc-Isoleucyl-Isoleucyl-Statyl (4-Hydroxybutyl)carboxamide

By the method described in Example 5c, the product of Example 5b (40 mg, 0.08 mmol) and 4-amino-1-butanol (7.7 µL, 84 µmol) were reacted to give crude material (32 mg, 70%). Flash chromatography eluting with 93.5/6.5 $CHCl_3$/EtOH afforded the title compound as a white solid (16 mg, 35%). $^1$H NMR ($CDCl_3+CD_3OD$, 300 MHz) δ 0.85–1.00 (m, 18H), 1.05–2.00 (m, 13H), 1.45 (s, 9H), 2.30 (m, 2H), 3.60–4.20 (m, 8H), 5.50 (d of d, 1H), 7.10 (m, 2H). Anal calcd for $C_{29}H_{56}N_4O_7 \cdot H_2O$: C, 58.96; H, 9.90; N, 9.48; Found: C, 58.67; H, 9.43; N, 9.26.

MS (FAB) m/e 573 (M+H)+, 595 (M+Na)+.

EXAMPLE 7

N-Boc-Isoleucyl-Isoleucyl-Statyl (5-Hydroxyamyl)carboxamide

By the method described in Example 5c, the product of Example 5b (40 mg, 0.08 mmol) and 5-amino-1-pentanol (8.6 mg, 84 µmol) were reacted to give crude material (41 mg, 87%). Flash chromatography eluting with 91.5/8.5 $CHCl_3$/EtOH afforded the title compound as a white solid (16 mg, 34%). $^1$H NMR ($CDCl_3+CD_3OD$, 300 MHz) δ 0.90 (m, 18H), 1.00–2.00 (m, 15H), 1.45 (s, 9H), 2.30 (m,2H), 3.20 (m, 2H), 3.60 (t, 2H), 3.85 (m, 3H), 4.15 (d of d, 1H).

Anal calcd. for $C_{30}H_{58}N_4O_7$: C, 61.40; H, 9.96; N, 9.55; Found: C, 61.15; H, 9.97; N, 9.38.

MS (FAB) m/e 587 (M+H)+.

EXAMPLE 8

N-Boc-Isoleucyl-Isoleucyl-Statyl (6-Hydroxyhexyl)carboxamide

By the method described in Example 5c, the product of Example 5b (40 mg, 0.08 mmol) and 6-amino-1-hexanol (9.8 mg, 84 µmol) were reacted to give crude product (40 mg, 83%). Flash chromatography eluting with 93.5/6.5 $CHCl_3$/EtOH afforded the title compound as a white solid (22 mg, 46%). $^1$H NMR ($CDCl_3+CD_3OD$, 300 MHz) δ 0.9 (m, 18H), 1.05–2.00 (m, 17H), 1.45 (s, 9H), 2.30 (m, 2H), 3.10–4.20 (m, 8H), 5.55 (m, exchangeable H), 7.05–7.22 (m, exchangeable H). Anal calcd for $C_{31}H_{60}N_4O_7$: C, 61.97; H, 10.07; N, 9.32; Found: C, 61.75; H, 9.82; N, 9.14. MS (FAB) m/e 601 (M+H)+, 623 (M+Na)+.

EXAMPLE 9

[1-[(N-Cbz-Isoleucyl-Isoleucyl) Amino]-3-methybutyl(methoxy)phosphinyl]acetic acid tert-Butyl ester

EXAMPLE 9A

[1-Amino-3-methybutyl(methoxy)phosphinyl]acetic acid tert-Butyl ester

[1-(Benzyloxycarbonyl)amino-3-methybutyl(methoxy)phosphinyl]acetic acid tert-butyl ester, prepared by the literature procedure: Bartlett, P. A.; Kezer, W. B.; J. Am. Chem. Soc., 106, 4282 (1984), (357 mg, 0.86 mmol) was dissolved in MeOH (11 mL) and hydrogenolyzed under $H_2$ using 10% Pd/C (84 mg) for approximately one hour. The catalyst was removed by filtration and the solvent removed under reduced pressure to give the title product as an oil (230 mg, 100%). The 300 MHz $^1$H NMR spectrum was found to be consistent with the proposed structure.

MS ($DCI/NH_3$) m/e 280 (M+H)+.

EXAMPLE 9B

[1-[(N-Cbz-Isoleucyl) Amino]-3-methybutyl (methoxy)phosphinyl]acetic acid tert-Butyl ester By the method described in Example 1e, the product of Example 9a (213 mg, 0.76 mmol) and Cbz-Ile-OH (203 mg, 0.76 mmol) were coupled. Normal work up afforded the title compound as an oil (402 mg, 100%). The 300 MHz $^1$H NMR spectrum was found to be consistent with the proposed structure.

MS ($DCI/NH_3$) m/e 393 (M+H)+, 410 (M+H+$NH_3$)+.

EXAMPLE 9C

[1-[(H-Isoleucyl) Amino]-3-methybutyl(methoxy)phosphinyl]acetic acid tert-Butyl ester The product of Example 9b (390 mg, 0.74 mmol) dissolved in MeOH (16 mL) was treated with 10% Pd/C (105 mg) under $H_2$ for 90 minutes. The catalyst was removed by filtration and the solution concentrated in vacuo to afford the title compound as an oil (260 mg, 90%). The 300 MHz $^1$H NMR spectrum was found to be consistent with the proposed structure.

MS ($DCI/NH_3$) m/e 527 (M+H)+, 544 (M+H+$NH_3$)+.

EXAMPLE 9D

[1-[(N-Cbz-Isoleucyl-Isoleucyl) Amino]-3-methybutyl(methoxy)phosphinyl]acetic acid tert-Butyl ester By the method described in Example 1e, the product of Example 9c (250 mg, 0.64 mmol) and Cbz-Ile-OH (170 mg, 0.64 mmol) were coupled. Normal work up afforded crude product which was purified by silica gel column chromatography eluting with 1% MeOH in $CHCl_3$ to afford the title compound (287 mg, 71%). $^1$H NMR ($CDCl_3$, 300 MHz) δ 0.9 (m, 18H), 1.00–2.00 (m, 9H), 1.45 (s, 9H), 2.95 (m, 2H), 3.75 (t, 3H), 4.00 (m, 1H), 4.4 (m, 1H), 4.6 (m, 1H), 5.10 (m, 2H), 5.5 (d of d, 1H), 6.40 (d of d, 1H), 6.90 (d of d, 1H), 7.35 (m, 5H). Anal calcd for $C_{32}H_{54}N_3O_8P$: C, 60.08; H, 8.51; N, 6.57; Found: C, 59.90; H, 8.52; N, 6.56.

MS (FAB) m/e 640 (M+H)+, 662 (M+Na)+.

EXAMPLE 10

N-Boc-Isoleucyl-Isoleucyl-Statyl-OH

EXAMPLE 10A

N-Boc-Isoleucyl-Isoleucyl Benzyl ester

To a solution of Boc-Ile-OH . 1/2$H_2O$ (3.00 g, 12.5 mmol) in THF (40 mL) cooled to −15° C. was added N-methylmorpholine (NMM) (1.51 mL, 1.39 g, 13.7 mmol) and isobutyl chloroformate (IBCF) (1.78 mL, 1.87 g, 13.7 mmol); the white suspension formed was stirred at −15° C. for 5 min and treated with a 0° C. solution of the p-toluene sulfonate salt of H-Ile-OBn (4.92 g, 12.5 mmol) and NMM (1.51 mL, 1.39 g, 13.7 mmol) in THF (10 mL)/dimethyl formamide (DMF) (5 mL). The reaction mixture was stirred at −15° C. and gradually allowed to warm to room temperature. After 4 hours, EtOAC was added; the mixture was washed with 1M H$_3$PO$_4$ (3×), saturated NaHCO$_3$ (2×), and brine, dried (MgSO$_4$), and concentrated in vacuo to give the title compound (5.16 g, 95%) as an oil which solidified on standing. The 300 MHz $^1$H NMR spectrum was found to be consistent with the proposed structure.

MS (DCI/NH$_3$) m/e 435 (M+H)$^+$, 452 (M+H+NH$_3$)$^+$.

EXAMPLE 10B

N-Boc-Isoleucyl-Isoleucyl-OH

A solution of the product of Example 10a (1.00 g, 2.30 mmol) in MeOH (25 mL) was treated with 10% Pd/C (0.50 g) and placed under H$_2$. After one hour, the catalyst was removed by filtration through Celite and the filtrate concentrated in vacuo. The residue obtained was dissolved in EtOAc, washed with 1M HCl and brine, dried (MgSO$_4$), and concentrated in vacuo to give the title compound (729 mg, 92%) as a colorless oil. The 300 MHz $^1$H NMR spectrum was found to be consistent with the proposed structure.

MS (DCI/NH$_3$) m/e 345 (M+H)$^+$, 362 (M+H+NH$_3$)$^+$.

EXAMPLE 10C

Statyl Ethyl ester HCl salt

A solution of the product of Example 1c (425 mg, 1.4 mmol) in HCl-HOAc (20 mL) was stirred at room temperature for 2 hours. Water was added and the solution lyophilized to give the title product as an oil (302 mg, 90%).

MS (DCI/NH$_3$) m/e 204 (M+H)$^+$.

EXAMPLE 10D

N-Boc-Isoleucyl-Isoleucyl-Statyl Ethyl ester

The product of Example 10c (150 mg, 0.63 mmol) and the product of Example 10b (150 mg, 0.62 mmol) were coupled by the method described in Example 1e to give the title compound (130 mg, 40%). The 300 MHz $^1$H NMR spectrum was found to be consistent with the proposed structure.

MS (DCI/NH$_3$) m/e 530 (M+H)$^+$, 547 (M+H+NH$_3$)$^+$.

EXAMPLE 10E

N-Boc-Isoleucyl-Isoleucyl-Statyl-OH

To a solution of the product of Example 10d (122 mg, 0.23 mmol) in MeOH (10 ml) at 0° C. was added a solution of 1M NaOH (0.5 mL, 0.5 mmol). The reaction mixture was stirred at 0° C. for 3 hours and concentrated in vacuo to remove the MeOH. EtOAc was added followed by washing with 1M H$_3$PO$_4$ and brine, drying (MgSO$_4$), and concentrating in vacuo to give a solid which was purified by flash chromatography on silica gel to give Boc-Ile-Ile-Sta-OMe. The 300 MHz $^1$H NMR spectrum was found to be consistent with the proposed structure. Anal calcd for C$_{26}$H$_{49}$N$_3$O$_7$: C, 60.56; H, 9.58; N, 8.15; Found: C, 60.35; H. 9.76; N. 8.14.

MS (DCI/NH$_3$) m/e 516 (M+H)$^+$, 533 (M+H+NH$_3$)$^+$.

To a solution of this compound (33 mg, 0.064 mmol) in MeOH (7 mL) was added 1N NaOH (0.,45 mL, 0.45 mmol); the reaction mixture was stirred overnight at room temperature. The MeOH was removed under reduced pressure, EtOAC was added, followed by 1M H$_3$PO$_4$ and brine washes, drying (MgSO$_4$), and concentrating in vacuo to give a white solid which was purified by preparative HPLC using a 1% TFA/H$_2$O and CH$_3$CN gradient. The fractions containing the desired product were concentrated to remove CH$_3$CN, frozen and lyophilized to give the title compound as a white solid (7 mg, 22%). $^1$H NMR (DMSO-d$_6$, 300 MHz) δ 0.80 (m, 18H), 1.00–1.75 (m, 9H), 1.37 (s, 9H), 2.05–2.40 (m, 2H), 3.60–3.90 (m, 3H), 4.15 (m, 1H), 4.15 (m, 1H), 6.77 (d, 1H) 7 65 (m, 2H) Anal calcd for C$_{25}$H$_{47}$N$_3$O$_7$ 0.25 trifluoroacetate (TFA): C, 57.77; H, 8.98; N, 7.93; Found: C, 57.77; H, 8.98; N, 8.05.

MS (FAB) m/e 502 (M+H)$^+$, 524 (M+Na)$^+$

EXAMPLE 11

N-Succinyl-Isoleucyl-Isoleucyl-Isoleucyl-Statyl-Valyl-OH

EXAMPLE 11A

Isoleucyl-Isoleucyl Benzyl ester HCl salt

A solution of the product of Example 10a (2.00 g, 4.61 mmol) in HCl-HOAc (25 mL) was stirred at room temperature for 2 hours. An additional aliquot of HCL-HOAc (10 mL) was added and stirring continued for an additional 4 hours. The reaction mixture was diluted with H$_2$O and lyophilized to give the title compound (1.67 g, 98%) as a white solid. The 300 MHz $^1$H NMR spectrum was found to be consistent with the proposed structure. MS (DCI/NH$_3$) m/e 335 (M+H)$^+$.

EXAMPLE 11B

N-(3-(Methoxycarbonyl)propionyl]-Isoleucyl-Isoleucyl Benzyl ester

A solution of Example the product of 11a (1.00 g, 2.70 mmol), N-methylmorpholine (NMM) (0.33 mL, 0.30 g, 3.00 mmol), methyl succinate (380 mg, 2.88 mmol), EDCI (570 mg, 2.97 mmol) and HOBT (450 mg, 3.33 mmol) in CH$_2$Cl$_2$ (50 mL) was stirred at 0° C. allowing to warm to room temperature overnight. The CH$_2$Cl$_2$ was removed under reduced pressure, EtOAc was added followed by 1M H$_3$PO$_4$ (3×), saturated NaHCO$_3$ (3×) and brine washes. Drying (MgSO$_4$) followed by concentration in vacuo afforded crude product which was purified by flash chromatography eluting with 3:1 then to 1:1 hexane/EtOAc to give the title compound (701 mg, 58%) as a white solid. The 300 MHz $^1$H NMR spectrum was found to be consistent with the proposed structure.

MS (DCI/NH$_3$) m/e 449 (M+H)$^+$, 466 (M+H+NH$_3$)$^+$.

EXAMPLE 11C

N-(3-(Methoxycarbonyl) propionyl)-Isoleucyl-Isoleucyl-OH

The product of Example. 11b (500 mg, 1.12 mmol) was debenzylated by the procedure described in Example 10b. The 300 MHz $^1$H NMR spectrum was found to be consistent with the proposed structure.

MS (DCI/NH$_3$) m/e 359 (M+H)$^+$, 376 (M+H+NH$_3$)$^+$.

EXAMPLE 11D

N-Boc-Statyl-OH

To a solution of the product of Example 1c (257 mg, 0.85 mmol) in MeOH (7 mL) was added a solution of 1M NaOH (1.7 mL, 1.7 mmol). The reaction mixture was stirred at room temperature for 2 hours and worked up by the procedure described in Example 2 to give the title compound (203 mg, 87%) as a white solid. The 300 MHz ¹H NMR spectrum was found to be consistent with the proposed structure.

MS (DCI/NH₃) m/e 276 (M+H)⁺, 293 (M+H+NH₃)⁺.

EXAMPLE 11E

N-Boc-Statyl-Valyl Benzyl ester

The product of Example 11d (150 mg, 0.59 μmol) and the p-toluene sulfonate salt of H-Val-OBn (212 mg, 0.56 mmol) were coupled by the method described in Example 1e to give the title compound (0.189 g, 75%). The 300 MHz ¹H NMR spectrum was found to be consistent with the proposed structure.

MS (DCI/NH₃) m/e 465 (M+H)⁺, 482 (M+H+NH₃)⁺.

EXAMPLE 11F

N-(3 -(Methoxycarbonyl) propionyl)-Isoleucyl-Isoleucyl-Statyl-Valyl Benzyl ester The product of Example 11e (125 mg, 0.27 mmol) was deprotected by the method described in Example 10c to give H-Sta-Val-OBn HCl (104 mg, 97%) as a white solid. The 300 MHz ¹H NMR spectrum was found to be consistent with the proposed structure. MS (DCI/NH₃) m/e 365 (M+H)⁺.

This dipeptide (83 mg, 0.21 mmol) was coupled with the product of Example 11c (84 mg, 0.23 mmol) by the method described in Example 1e to give crude material which was purified by flash chromatography on silica gel eluting with 3% MeOH/CHCl₃ to give the title compound (11 mg, 80%). The 300 MHz ¹H NMR spectrum was found to be consistent with the proposed structure.

MS (DCI/NH₃) m/e 705 (M+H)⁺.

EXAMPLE 11G

N-Succinyl-Isoleucyl-Isoleucyl-Statyl-Valyl-OH

The product of Example 11f (100 mg, 0.14 mmol) was debenzylated by catalytic hydrogenation by the method described in Example 10b and purified by preparative HPLC to give the carboxylic acid. The 300 MHz ¹H NMR spectrum was found to be consistent with the proposed structure. Anal calcd for $C_{30}H_{54}N_4O_9 \cdot 0.7$ TFA: C, 54.30; H, 7.94; N, 8.07; Found: C, 54.44; H, 8.06; N, 8.32.

MS (FAB) m/e 615 (M+H)⁺, 637 (M+Na)⁺.

To a solution of the carboxylic acid (69 mg, 0.113 mmol) in CH₃OH (5 mL) at 0° C. was added 1M NaOH (0.23 mL, 0.23 mmol). The reaction mixture was stirred at 0° C. allowing to warm to room temperature overnight. An additional aliquot of 1M NaOH (0.1 mL, 0.1 mmol) was added and the reaction mixture again stirred overnight. The CH₃OH was removed under reduced pressure, H₂O was added, and the solution was lyophilized. The material obtained was dissolved in H₂O/acetone, filtered, and lyophilized to give the title compound (38.7 mg, 57%). ¹H NMR (DMSO-d₆, 300 MHz) δ 0.85 (m, 24H), 1.00–1.75 (m, 13H), 2.00–2.55 (m, 6H), 3.65–3.90 (m, 2H), 4.15 (m, 3H), 7.5–7.9 (m, 4H). Anal calcd for $C_{29}H_{52}N_4O_9$ 0.4 TFA 1.0 H₂O: C, 53.87; H, 8.25; N, 8.43; Found: C, 53.87; H. 7.95; N. 8.62.

MS (DCI/NH₃) m/e 601 (M+H)⁺.

EXAMPLE 12

N-Boc-Cyclohexylalanyl-Isoleucyl-Statyl Ethyl ester

EXAMPLE 12A

N-Doc-Cyclohexylalanyl-Isoleucyl Benzyl ester

Boc-Cha-OH (3.5 g, 12.9 mmol) and the p-toluene sulfonate salt of H-Ile-OBn (5.08 g, 12.9 mmol) were coupled using the method described in Example 10a to give crude material which was purified by flash chromatography on silica gel eluting with 15% EtOAc/hexane to give pure title compound. The 300 MHz ¹H NMR spectrum was found to be consistent with the proposed structure.

MS (DCI/NH₃) m/e 474 (M+H)⁺, 492 (M+H+NH₃)⁺.

EXAMPLE 12B

N-Boc-Cyclohexylalanyl-Isoleucyl-Statyl Ethyl ester

The product of Example 12a (500 mg, 1.055 mmol) was debenzylated using the method described in Example 10b to give the free carboxylic acid (405 mg, 100%). The 300 MHz ¹H NMR spectrum was found to be consistent with the proposed structure.

MS (DCI/NH₃) m/e 385 (M+H)⁺, 402 (M+H+NH₃)⁺.

The carboxylic acid (172 mg, 0.45 mmol) and the product of Example 10c (107 mg, 0.45 mmol) were coupled using the method described in Example 1e crude product (232 mg, 91%). Flash chromatography on silica gel using 3:1 hexane/EtOAc afforded the title compound (146 mg, 57%. ¹H NMR (DMSO-d₆, 300 MHz) δ 0.8 (m, 15H), 1.0–1.73 (m, 19H), 1.40 (s, 9H), 2.15–2.43 (m, 2H), 3.65–4.20 (m, 6H), 4.90 (d of d, 1H), 6.93 (d of d, 1H), 7.60 (d of t, 2H). Anal calcd for $C_{30}H_{55}N_3O_7$: C, 63.27; H, 9.70; N, 7.38; Found: C, 63.14; H, 9.71; N, 7.34.

MS (FAB) m/570 (M+H)⁺.

EXAMPLE 13

N-Boc-Isoleucyl-Isoleucyl-Statyl-β-Alanyl Ethyl ester

EXAMPLE 13A

N-Boc-Statyl-β-Alanyl Ethyl ester

The product of Example 11d (292 mg, 1.06 mmol) and β-Ala-OEt (196 mg, 1.27 mmol) were coupled by the method described in Example 10a to give the title compound (355 mg, 89%) as a white solid.

The 300 MHz ¹H NMR spectrum was found to be consistent with the proposed structure.

MS (DCI/NH₃ ) m/e 375 (M+H)⁺.

EXAMPLE 13B

N-Boc-Isoleucyl-Isoleucyl-Statyl-β-Alanyl Ethyl ester

The product of Example 13a (343 mg, 0.92 mmol) was deprotected by the method described in Example 1d to give the HCl salt (279 mg, 98%). The 300 MHz ¹H NMR spectrum was found to be consistent with the proposed structure. MS (DCI/NH₃) m/e 274.

The HCl salt (164 mg, 0.53 mmol) was coupled with the product of Example 10b (200 mg, 0.58 mmol) by the method described in Example 10a to give crude material (284 mg, 82%). Flash chromatography on silica gel eluting with 2% CH₃OH/CHCl₃ afforded the title compound (141 mg, 41%) as a white solid.

¹H NMR (DMSO-d₆, 300 MHz) δ 0.80 (m, 18H), 1.17 (t, 3H), 1.37 (s, 9H), 1.00–1.70 (m, 9H), 2.10 (m, 2H), 2.40 (t, 2H), 3.15–3.35 (m, 2H), 3.65 (m, 1H), 3.80 (bt, 2H), 4.03 (q, 2H), 4.15 (m, 1H), 4.75 (d of d, 1H), 6.75 (d, 1H), 7.47–7.82 (m, 3H). Anal calcd for $C_{30}H_{56}N_4O_8$: C, 60.00; H, 9.36; N, 9.33; Found: C, 59.98; H, 9.40; N, 9.33.

MS (FAB) m/e 601 (M+H)⁺.

EXAMPLE 14A

N-Boc-Statyl Isobutylcarboxamide

The product of Example 11d (260 mg, 0.94 mmol) was coupled with isobutylamine (113 μL, 83 mg, 1.14 mmol) using the method described in Example 10a to give the title compound (280 mg, 90%) as a white solid. The 300 MHz ¹H NMR spectrum was found to be consistent with the proposed structure.

MS (DCI/NH₃) m/e 331 (M+H)⁺.

EXAMPLE 14B

N-Boc-Isoleucyl-Isoleucyl-Statyl Isobutylcarboxamide

The product of Example 14a (233 mg, 0.706 mmol) was deprotected by the method described in Example 1d to give the HCl salt (188 mg, 100%). The 300 MHz ¹H NMR spectrum was found to be consistent with the proposed structure.

MS (DCI/NH₃) m/e 231 (M+H)⁺.

The HCl salt (90 mg, 0.34 mmol) was coupled with the product of Example 10b (128 mg, 0.37 mmol) by the method described in Example 10a to give crude material (119 mg, 63%). Flash chromatography on silica gel eluting with 2% CH₃OH in CHCl₃ gave pure title compound (27 mg, 14%) as a white solid. ¹H NMR (DMSO-d₆, 300 MHz) δ 0.80 (m, 24H), 1.35 (s, 9H), 1.00–1.85 (m, 10H), 2.10 (m, 2H), 2.85 (m, 2H), 3.75 (m, 3H), 4.26 (m, 1H), 4.77 (m, 1H), 6.75–6.95 (d of d, 1H), 7.40–7.70 (m, 3H). Anal calcd for $C_{29}H_{56}N_4O_6$ 0.5 H₂O: C, 61.56; H, 10.15; N, 9.90; Found: C, 61.49; H, 10.03; N, 9.86.

MS (FAB) m/e 557 (M+H)⁺.

EXAMPLE 15

N-Boc-Cyclohexylalanyl-Isoleucyl-Statyl-OH

The product of Example 12b (85 mg, 0.15 mmol) was hydrolyzed by the method described in Example 2 to give the title compound.

¹H NMR (DMSO-d₆, 300 MHz) δ 0.80 (m, 12H), 1.35 (s, 9H), 1.00–1.73 (m, 19H), 2.10–2.30 (m, 2H), 3.67 (m, 1H), 3.83 (m, 1H), 3.95 (m, 1H), 4.13 (m, 1H), 6.92 (m, 1H), 7.43–7.65 (m, 2H). Anal calcd for $C_{28}H_{51}N_3O_7$ 0.5 H₂O: C, 61.07; H, 9.52; N, 7.63; Found: C, 61.47; H, 9.49; N, 7.63.

MS (FAB) m/e 542 (M+H)⁺, 564 (M+Na)⁺.

EXAMPLE 16

N-Boc-Isoleucyl-Isoleucyl-Statyl-β-Alanyl-OH

The product of Example 13 (100 mg, 0.17 mmol) was hydrolyzed by the method described in Example 2 to give the title compound (68.7 mg, 71%) as a white solid. ¹H NMR (DMSO-d₆, 300 MHz) δ 0.80 (m, 18H), 1.00–1.73 (m, 9H), 1.40 (s, 9H), 2.10 (m, 2H), 2.35 (t, 2H), 3.20 (m, 2H), 3.66 (m, 1H), 3.80 (bt, 2H), 4.15 (m, 1H), 4.75 (bd, 1H), 6.75 (d, 1H), 7.45–7.80 (m, 3H), 12.15 (bs, 1H). Anal calcd for $C_{28}H_{52}N_4O_8$: C, 58.72; H, 9.15; N, 9.78; Found: C, 58.47; H, 9.21; N, 9.67.

MS (FAB) m/e 573 (M+H)⁺.

EXAMPLE 17

N-Boc-Isoleucyl-Isoleucyl-Tryptophanyl Carboxaldehyde

EXAMPLE 17A

Tryptophanyl (N-Methoxy-N-methyl)carboxamide HCl salt

To Boc-Trp-OH (5.00 g, 16.4 mmol) dissolved in CH₂Cl₂ (100 mL) containing triethylamine (TEA) (2.75 mL, 1.2 equiv.) was added benzotriazol-1-yloxy-tris (dimethylamino) phosphonium hexafluorophosphate (BOP-reagent) (8.72 g, 1.2 equiv.), N,O-dimethylhydroxylamine hydrochloride (1.92 g, 1.2 equiv.), and TEA (2.75 mL, 1.2 equiv.). After one hour of stirring at room temperature, CH₂Cl₂ (50 mL) was added and the mixture washed with 10% citric acid, saturated NaHCO₃, and brine, dried (Na₂SO₄), and concentrated in vacuo to afford a yellow oil which was crystallized from EtOAc/hexane. The Boc-protecting group was removed by the method described in Example 1d to afford the title compound (5.02 g, 91%). The 300 MHz ¹H NMR spectrum was found to be consistent with the proposed structure.

EXAMPLE 17B

N-Boc-Isoleucyl-Tryptophanyl (N-Methoxy-N-methyl) carboxamide

The product of Example 17a (2.45 g, 8.6 mmol) and Boc-Ile-OH (2.07 g, 8.6 mmol) were coupled using the procedure described in Example 10a to give crude material which was purified by flash chromatography on silica gel eluting with 1:1 EtOAc/hexane to afford the title compound (3.5 g, 88%).

The 300 MHz ¹H NMR spectrum was found to be consistent with the proposed structure.

MS (FAB) m/e 4 61 (M+H)⁺.

EXAMPLE 17C

N-Boc-Isoleucyl-Isoleucyl-Tryptophanyl (N-Methoxy-N-methyl)carboxamide

The Boc protecting group was removed from the product of Example 17b by the method described in Example 1d to afford the hydrochloride salt (604 mg, 1.53 mmol). This compound was coupled with Boc-Ile-OH hemihydrate (368 mg, 1.0 equiv.) by the method described in Example 10a to give crude product. Purification by flash chromatography on silica gel using 1:1 EtOAc/hexane afforded the title compound (576 mg, 66%). The 300 MHz ¹H NMR spectrum was found to be consistent with the proposed structure. Further purification was obtained by preparative reverse phase HPLC eluting with 0.1% TFA/H₂O and CH₃CN. Anal calcd for $C_{30}H_{47}N_5O_6$ 0.25 TFA: C, 60.83; H, 7.91; N, 11.63; Found: C, 60.86; H, 8.05; N, 11.75.

MS (FAB) m/e 574 (M+H)⁺.

EXAMPLE 17D

N-Boc-Isoleucyl-Isoleucyl-Tryptophanyl Carboxaldehyde

To the product of Example 17c (100 mg, 0.1745 mmol) dissolved in THF (8 mL) under N₂ and cooled to 0° C. in an ice bath was added 1M lithium aluminum hydride (LAH) in THF (1.40 mL, 8.0 equiv). After 20 minutes at 0° C., the reaction mixture was poured into 10% citric acid (10 mL). After stirring at room temperature for 30 minutes, 10% citric acid (10 mL) was added and the mixture was extracted with EtOAc (3×15 mL). The combined organic extracts were washed with saturated NaHCO$_3$, 10% citric acid, and brine, dried (Na$_2$SO$_4$), and concentrated in vacuo to give a semi-solid residue. This crude product was flash chromatographed on silica gel using 1:1 EtOAc/hexane as the eluant to give the title compound (16 mg, 18%). $^1$H NMR (CDCl$_3$, 300 MHz) δ 0.90 (m, 12H), 1.05–2.00 (m 6H), 1.45 (s, 9H), 3.30 (bt, 2H), 3.90 (m, 1H), 4.30 (m, 1H), 4.90 (m, 1H), 6.45 (bd, 1H), 6.60 (bs, 1H), 7.00–7.40 (m, 5H), 7.60 (bd, 1H), 8.20 (bs, 1H), 9.62 (s, 1H). Anal calcd for C$_{28}$H$_{42}$N$_4$O$_5$: C, 65.35; H, 8.23; N, 10.89; Found: C, 65.44; H, 8.53; N, 10.45.

MS (FAB) m/e 515 (M+H)$^+$, 537 (M+Na)$^+$.

EXAMPLE 18

(4S)-4-(N-Boc-Isoleucyl-Isoleucyl-Amino)-5-(3-indolyl)-3-hydroxypentanoic acid

EXAMPLE 18A

N-Boc-Tryptophanyl-[3,5-dimethylpyrazolide]

Boc-Trp-OH (6.00 g, 24.3 mmol) was reacted with 3,5-dimethylpyrazole (2.33 g, 1 equiv) by the method described in Example 1a to give crude material which was flash chromatographed on silica gel eluting with 2:1 hexane/EtOAc to give the title compound (6.95 g, 75%). The 300 MHz $^1$H NMR spectrum was found to be consistent with the proposed structure.

EXAMPLE 18B

N-Boc-Tryptophanyl Carboxaldehyde

The product of Example 18a (4.00 g, 10.47 mmol) was reduced by the method described in Example 1b to give crude aldehyde which was purified by by flash chromatography on silica gel eluting with 2:1 hexane/EtOAc to give the title compound (2.44 g, 81%).

The 300 MHz $^1$H NMR spectrum was found to be consistent with the proposed structure.

EXAMPLE 18C (4S)-4-N-Boc-Amino-5-(3-indolyl)-3-hydroxypentanoic acid Ethyl ester Using the procedure described in Example 1c, the product of Example 18b (2.44 g, 8.46 mmol) was converted to crude product which was purified by flash chromatography on silica gel eluting with 2:1 hexane/EtOAc to afford the title compound (1.91 g, 60%).

The 300 MHz $^1$H NMR spectrum was found to be consistent with the proposed structure.

EXAMPLE 18D (4S)-4-(N-Boc-Isoleucyl-Isoleucyl-Amino)-5-(3-indolyl)-3-hydroxypentanoic acid Ethyl ester The product of Example 18c (1.00 g, 2.66 mmol) was deprotected using the procedure described in Example 1d to give the hydrochloride salt (786 mg, 95%). This hydrochloride salt (604 mg, 1.94 mmol) was converted to its free base using saturated NaHCO$_3$ (50 mL) and extracted after 30 minutes using EtOAc. The EtOAc was removed under reduced pressure to afford the free base as an oil.

To the product of Example 10b (666 mg, 1 equiv) dissolved in CHCl$_3$ (8 mL) was added EDCI (445.6 mg, 1.2 equiv) and HOBT (314 mg, 1.2 equiv). After stirring for 30 minutes, the free amine in CHCl$_3$ (2 mL)/DMF (3 mL) was added and the reaction mixture was allowed to stir at room temperature overnight. The reaction mixture was concentrated in vacuo and EtOAc was added. Washing with saturated NaHCO$_3$, H$_2$O, 1N H$_3$PO$_4$, and brine, drying (Na$_2$SO$_4$), and concentrating under reduced pressure afforded the product as an oil which was purified by flash chromatography on silica gel eluting with 1:1 EtOAc/hexane to give the title product (381 mg, 33%). The 300 MHz $^1$H NMR spectrum was found to be consistent with the proposed structure.

MS (FAB) m/e 603 (M+H)$^+$.

EXAMPLE 18E (4 S)-4-(N-Boc-Isoleucyl-Isoleucyl-Amino)-5-(3-indole)-3-hydroxypentanoic acid The product of Example 18d (61 mg, 101.3 mmol) was hydrolyzed using the method described in Example 2 to give crude material which was purified by preparative HPLC to give the title compound. $^1$H NMR (CDCl$_3$+CD$_3$OD, 300 MHz) δ 0.70–1.00 (m, 12H), 1.00–1.90 (m, 6H), 1.45 (s, 9H), 1.70 (m, 2H), 2.30 (m, 2H), 2.90–3.15 (m, 2H), 3.97 (m, 3H), 4.32 (bd, 1H), 7.10 (m, 3H), 7.33 (d, 1H), 7.70 (bt, 1H). Anal calcd for C$_{30}$H$_{46}$N$_4$O$_7$ 0.7 TFA: C, 57.62; H, 7.19; N, 8.56; Found: C, 57.49; H, 7.25; N, 8.94.

MS (DCI/NH$_3$) m/e 575 (M+H)$^+$, 592 (M+H+NH$_3$)$^+$.

EXAMPLE 19

(4S]-4-(N-Succinyl-Isoleucyl-Isoleucyl-Amino)-5-(3-indolyl)-3-hydroxypentanoic acid Ethyl ester The product of Example 18d (41.1 mg, 68.3 mmol) was deprotected using the method described in Example 1d to give the hydrochloride salt. To this hydrochloride salt dissolved in DMF (1 mL) was added 4-(dimethylamino)-pyridine (DMAP) (20 mg), triethylamine (TEA) (5 drops), and succinic anhydride (8.2 mg, 1.2 equiv). The reaction mixture was stirred overnight at room temperature and concentrated under reduced pressure. The residue was purified by preparative HPLC to afford the title compound $^1$H NMR (CDCl$_3$, 300 MHz) δ 0.85 (m, 12H), 1.00–2.10 (m, 12H), 1.23 (t, 3H), 2.40–3.10 (m, 4H), 3.03 (d of d, 1H), 3.70 (m, 1H), 4.12 (q, 2H), 4.00–4.50 (m, 2H), 6.30–7.30 (m, 5H), 7.33 (bd, 1H), 7.66 (bd, 1H), 8.10 (bs, 1H). Anal calcd for C$_{31}$H$_{46}$N$_4$O$_8$ 0.75 TFA: C, 56.72; H, 6.85; N, 8.14; Found: C, 57.08; H, 7.01; N,8.18.

MS (FAB) m/e 603 (M+H)$^+$.

EXAMPLE 20

N-[(4S)-4-(N-Boc-Isoleucyl-Isoleucyl-Amino)-5-(3-indolyl)-3-hydroxypentanoyl]-Valyl-OH

EXAMPLE 20A

N-[(4S)-4-(N-Boc-Amino)-5-(3-indolyl)-3-hydroxypentanoyl]Valyl Benzyl ester

The product of Example 18c (90.2 mg, 0.24 mmol) was hydrolyzed by the procedure described in Example 2 to give crude product which was purified by preparative HPLC to give the desired carboxylic acid. The 300 MHz $^1$H NMR spectrum was found to be consistent with the proposed structure. MS (DCI/NH$_3$) m/e 349 (M+H)$^+$, 366 (M+H+NH$_3$)$^+$.

This carboxylic acid (83.6 mg, 0.24 mmol) was coupled with the p-toluene sulfonate salt of Val-OBn (91.2 mg, 1.0 equiv) by the procedure described in Example

EXAMPLE 20B

N-[(4S)-4-(N-Boc-Isoleucyl-Amino)-5-(3-indolyl)-3-hydroxypentanoyl]-Valyl Benzyl ester The product of Example 20a was deprotected by the method described in Example 1d to give the hydrochloride salt. This salt (205 mg, 0.434 mmol) was coupled with Boc-Ile-OH hemihydrate (104 mg, 1.0 equiv) by the method described in Example 1e to give a semi-solid residue which was purified by flash chromatography on silica gel eluting with 1:1 EtOAc/hexane to give after crystallization from 1:1 EtOAc/hexane the title compound (197 mg, 70%). The 300 MHz $^1$H NMR spectrum was found to be consistent with the proposed structure. Anal calcd for $C_{36}H_{50}N_4O_7$ 0.25 TFA: C, 64.54; H, 7.46; N, 8.25; Found: C, 64.76; H, 7.11; N, 8.25. MS (DCI/NH$_3$) m/e 651 (M+H)$^+$.

EXAMPLE 20C

N-[(4S)-4-(N-Boc-Isoleucyl-Isoleucyl-Amino)-5-(3-indolyl)-3-hydroxypentanoyl]-Valyl Benzyl ester The product of Example 20b (104 mg, 0.16 mmol) was deprotected by the method described in Example 1d to give the hydrochloride salt. This salt was coupled with Boc-Ile-OH hemihydrate (38.4 mg, 1.0 equiv) by the method described in Example 1e and purified by the method described in Example 20b to give the title compound (58 mg, 47%). The 300 MHz $^1$H NMR spectrum was found to be consistent with the proposed structure, Anal calcd for $C_{42}H_{61}N_5O_8$ 0.8 EtOAc: C, 65.12; H, 8.14; N, 8.44; Found: C, 65.18; H, 7.87; N 8.86

MS (DCI/NH$_3$) m/e 764 (M+H)$^+$, 781 (M+H+NH$_3$)$^+$.

EXAMPLE 20D

N-[(4S)-4-(N-Boc-Isoleucyl-Isoleucyl-Amino)-5-(3-indolyl)-3-hydroxypentanoyl]-Valyl-OH To 10% Pd/C (21 mg) in acetic acid (HOAc) under N$_2$ was added ammonium formate (10.8 mg, 3 equiv). After 10 minutes, the product of Example 20c (43.4 mg, 56.9 μmol) was added in HOAc (3 mL). The reaction mixture was stirred overnight at room temperature. The catalyst was removed by filtration and the HOAc removed under reduced pressure. The residue was taken up in H$_2$O/CH$_3$CN and lyophilized to afford the title compound. $^1$H NMR (DMSO-d$_6$, 300 MHz) δ 0.80 (m, 18H), 1.00–1.50 (m, 3H), 1.35 (s, 9H), 1.70 (m, 2H), 2.00 (m, 2H), 2.30 (m, 1H), 2.70 (m, 1H), 3.00 (m, 1H), 3.70–4.30 (m, 6H), 6.80–7.90 (m, 6H), 10.70 (m, 1H). Anal calcd for $C_{35}H_{55}N_5O_8$ 0.5 TFA: C, 58.58; H, 7.55; N, 9.44; Found: C, 58.67; H, 7.64; N, 9.34.

MS (FAB) m/e 674 (M+H)$^+$ 696 (M+Na)$^+$.

EXAMPLE 21

N-[(4S)-4-(N-Boc-Aspartyl-Isoleucyl-Isoleucyl-Amino)-5-(3-indolyl)-3-hydroxypentanoyl]-Valyl-OH

EXAMPLE 21A

N-[(4S)-4-(N-Boc-Aspartyl(β-O-Benzyl)-Isoleucyl-Isoleucyl-Amino)-5-(3-indolyl)-3-hydroxypentanoyl]-Valyl Benzyl ester The product of Example 20c (60.8 mg, 79.7 μmol) was deprotected using the method described in Example 1d to give the hydrochloride salt. This salt was coupled with Boc-Asp(βOBn)-OH (30.9 mg, 1.2 equiv) by the method described in Example 1e to give crude material which was purified by flash chromatography on silica gel eluting with 1:1 EtOAc/hexane to give the title product (25.1 mg, 33%).

EXAMPLE 21B

N-[(4S)-4-(N-Boc-Aspartyl-Isoleucyl-Isoleucyl-Amino)-5-(3-indolyl)-3-hydroxypentanoyl]-Valyl-OH Catalytic transfer hydrogenation of the product of Example 21a (25.1 mg, 26 μmol) by the method described in Example 20d afforded after preparative HPLC and lyophilization the title compound. $^1$H NMR (CDCl$_3$+CD$_3$OD, 300 MHz) δ 0.74–1.00 (m, 18H), 1.45 (s, 9H), 1.85 (m, 1H), 2.00 (m, 1H), 2.10–2.50 (m, 4H), 2.60–3.20 (m, 10H), 3.95–4.50(m, 10H), 6.90–7.15 (m, 6H), 7.60 (m, 1H). Anal calcd for $C_{39}H_{60}N_6O_{11}$ 1.0 TFA: C, 54.54; H, 6.81; N, 9.31; Found: C, 54.32; H, 6.78; N, 9.38.

MS (FAB) m/e 789 (M+H)$^+$, 811 (M+Na)$^+$, 833 (M+2Na-H)$^+$.

EXAMPLE 22

(4S)-4-(N-Boc-Cyclohexylalanyl-Isoleucyl-Amino)-5-(3-indolyl)-3-hydroxypentanoic acid

EXAMPLE 22A (4S)-4-(N-Boc-Cyclohexylalanyl-Isoleucyl-Amino)-5-3-indolyl)-3-hydroxypentanoic acid Ethyl ester The product of Example 18c (255 mg, 0.678 mmol) was deprotected by the method described in Example 1d and converted to its free base as described in Example 18d. The product of Example 12a was debenzylated as described in Example 12b to give the carboxylic acid. The free amine was coupled with the carboxylic acid (312.4 mg, 1.2 equiv) by the method described in Example 1e to give, after flash chromatography on silica gel using 1:1 EtOAc/hexane as the eluant, the title compound (337 mg, 90%). The 300 MHz $^1$H NMR spectrum was found to be consistent with the proposed structure.

MS (DCI/NH$_3$) m/e 643 (M+H)$^+$.

EXAMPLE 22B (4 S)-4-(N-Boc-Cyclohexylalanyl-Isoleucyl-Amino)-5-3-indolyl)-3-hydroxypentanoic acid The product of Example 22a (50 mg, 0.078 mmol) was hydrolyzed by the method described in Example 2 to give after preparative HPLC the title compound. $^1$H NMR (CDCl$_3$, 300 MHz) δ 0.70–1.05 (m, 6H), 1.40 (2s, 9H), 1.05–2.60 (m, 13H), 3.1 (m, 2H), 4.00–4.45 (m, 3H), 4.90 (m, 1H), 6.60–7.20 (m, 4H), 7.33 (d, 1H), 7.60 (2d, 2H), 8.20 (m, 1H). Anal calcd for $C_{33}H_{50}N_4O_7$ 0.65

TFA: C, 59.80; H, 7.41; N, 8.13; Found: C, 59.82; H, 7.37; N, 8.14.

MS (FAB) m/e 615 (M+H)+, 637 (M+Na)+.

EXAMPLE 23

N-[(4S)-4-(N-Boc-Cyclohexylalanyl-Isoleucyl-Amino)-5-(3-indolyl)-3-hydroxypentanoyl]-Valyl-OH

EXAMPLE 23A

N-[(4S)-4-(N-Boc-Cyclohexylalanyl-Isoleucyl-Amino)-5-(3-indolyl)-3-hydroxypentanoyl]-Valyl Benzyl ester The product of Example 20a (493 mg, 0.918 mmol) was deprotected by the method described in Example 1d to give the hydrochloride salt. The product of Example 12a was debenzylated as described in Example 12b to give the carboxylic acid (423 mg, 1.2 equiv). The amine hydrochloride salt and the carboxylic acid were coupled using the method described in Example 1e to give, after flash chromatography on silica gel eluting with 1:1 EtOAc/hexane, the title compound (217 mg, 30%). The 300 MHz $^1$H NMR spectrum was found to be consistent with the proposed structure.

EXAMPLE 23B

N-[(4S)-4-(N-Boc-Cyclohexylalanyl-Isoleucyl-Amino)-5-(3-indolyl)-3-hydroxypentanoyl]-Valyl-OH Catalytic transfer hydrogenation of the product of Example 23a (40 mg, 0.05 mmol) by the method described in Example 20d afforded, after preparative HPLC, the title compound. $^1$H NMR (CDCl3, 300 MHz) δ 0.65 (m, 6H), 1.02 (t, 6H), 0.85–1.50 (m, 6H), 1.45 (2s, 9H), 1.70 (m, 7H), 2.25 (m, 2H), 2.30–3.20 (m, 4H), 3.40 (m, 1H), 4.03 (m, 2H), 4.20 (m, 1H), 4.35 (m, 2H), 4.95 (m, 1H), 6.60 (bs, 1H), 6.90–7.50 (m, 1H), 8.40 (m, 10H). Anal calcd for $C_{38}H_{59}N_5O_8$ 0.6 TFA: C, 60.18; H, 7.68; N, 8.95; Found: C, 60.35; H, 7.74; N, 9.06.

MS (FAB) m/e 714 (M+H)+, 736 (M+Na)+.

EXAMPLE 24

(2S,3R,4S)-2-(N-Boc-Isoleucyl-Isoleucyl-Amino)-1-cyclohexyl-3,4-dihydroxy-6-methylheptane

EXAMPLE 24A (2S,3R,4S)-2-Amino-1-cyclohexyl-3,4-dihydroxy-6-methylheptane (2S,3R,4S)-2-[(tert-Butyloxycarbonyl) amino]-1-cyclohexyl-3,4 -dihydroxy-6-methylheptane was prepared as described in the literature: Luly, J. R.; Hsiao, C. N.; BaMaung, N.; Plattner, J. J. J. Org. Chem. 1988, 53, 6109. This compound (413 mg, 1.2 mmol) was deprotected by the method described in Example 1d to give the hydrochloride salt, which was dissolved in THF (2 mL) and treated with 1N NaOH to pH 12. The mixture was extracted with CH2Cl2 (5×5 mL). The combined organic extracts were dried (K2CO3) and concentrated in vacuo to afford the title compound (294 mg, 99%). The 300 MHz $^1$H NMR spectrum was found to be consistent with the proposed structure.

EXAMPLE 24B (2S,3R,4S)-2-(N-Boc-Isoleucyl-Amino)-1-cyclohexyl-3,4-dihydroxy-6-methylheptane The product of Example 24a (330 mg, 1.42 mmol) and Boc-Ile-OH hemihydrate (342 mg, 1.42 mmol) were coupled by the procedure described in Example 10a to give the title compound (558 mg, 86%). $^1$H NMR (CDCl3+CD3OD, 300 MHz) δ 0.85–1.00 (m, 12H), 1.10–2.00 (m, 19H), 1.45 (s, 9H), 3.20 (d of d, 1H), 3.30 (d of t, 1H), 3.92 (t, 1H), 4.36 (d of t, 1H), 4.90 (bs, 1H), 6.20 (d, 1H). Anal calcd for $C_{25}H_{48}N_2O_5$ 0.25 H2O: C, 65.11; H, 10.60; N, 6.07; Found: C, 65.09; H, 10.48; N, 6.03.

MS (FAB) m/e 457 (M+H)+.

EXAMPLE 24C (2S,3R,4S)-2-(N-Boc-Isoleucyl-Isoleucyl-Amino)-1-cyclohexyl-3,4-dihydroxy-6-methylheptane The product of Example 24b (156 mg, 0.34 mmol) was deprotected by the method described in Example 1d to give the hydrochloride salt. The salt was converted to its free base using the procedure described in Example 24a to give the free amine (121 mg, 100%). The 300 MHz $^1$H NMR spectrum was found to be consistent with the proposed structure.

MS (DCI/NH3) m/e 357 (M+H)+.

To a stirred solution of Boc-Ile-OH hemihydrate (81 mg, 0.34 mmol) in THF (2 mL) at −20° C. was added NMM (37 μL, 0.34 mmol) followed by IBCF (44 μL, 0.34 mmol) maintaining the temperature at or below −17° C. After 20 minutes, a solution of the free base from above in THF (2 mL) was added continuing to maintain the temperature below −17° C. The reaction mixture was then allowed to warm to room temperature overnight. The solvent was removed under reduced pressure and the residue partitioned between EtOAc and saturated NaHCO3. The organic phase was washed with 1N H3PO4 and brine, dried (MgSO4), and concentrated in vacuo to afford a residue which was crystalized from 1:1 THF/EtOAc to give the title compound (181 mg, 93%). mp 178°–179° C. $^1$H NMR (CDCl3, 300 MHz) δ 0.94 (m, 18H), 1.00–2.25 (m, 13H), 1.45 (s, 9H), 3.18 (t, 1H), 3.35 (m, 1H), 3.88 (t, 1H), 4.22–4.45 (m, 3H), 5.02 (bs, 1H), 6.56 (bs, 1H), 6.80 (bd, 1H). Anal calcd for $C_{31}H_{59}N_3O_6$: C, 65.37; H, 10.40; N, 7.38; Found: C, 65.02; H, 10.13; N, 7.38.

MS (DCI/NH3) m/e 570 (M+H)+, 587 (M+H+NH3)+.

EXAMPLE 25

(2S,3R,4S)-2-(N-Succinyl-Isoleucyl-Isoleucyl-Amino)-1-cyclohexyl-3,4-dihydroxy-6-methylheptane The product of Example 24c (67 mg, 0.11 mmol) was deprotected by the method described in Example 1d to give the hydrochloride salt. The salt was converted to its free base using the procedure described in Example 24a to give the free amino compound (55 mg, 100%). The 300 MHz $^1$H NMR spectrum was found to be consistent with the proposed structure. MS (DCI/NH3) m/e 470 (M+H)+.

The amine (50 mg, 0.10 mmol) was reacted with succinic anhydride (12 mg, 0.127 mmol, 1.2 equiv) by the method described in Example 19 to give the title compound. mp 253°–254° C. $^1$H NMR (DMSO-d6, 300 MHz) δ 0.70–1.00 (m, 18H), 1.00–1.83 (m, 22H), 2.40 (m, 4H), 2.92 (bd, 1H), 3.09 (bt, 1H), 4.05–4.25 (m, 3H), 4.49 (bd, 1H), 4.70 (bs, 1H), 7.52 (d, 1H), 7.80 (d, 1H), 7.92 (d, 1H). Anal calcd for $C_{30}H_{55}N_3O_7$ H2O: C, 61.30; H, 9.77; N, 7.15; Found: C, 60.95; H, 9.30; N, 7.19.

MS (FAB) m/e 570 (M+H)+, 592 (M+Na)+.

EXAMPLE 26

(2S,3R,4S)-2-(N-BOC-Aspartyl(β-O-Benzyl)-Isoleucyl-Isoleucyl -Amino)-1-cyclohexyl-3,4-dihydroxy-6-methylheptane The product of Example 24c was deprotected and converted to its free base by the method described in Example 25 to give the amino compound. The amino compound (100 mg, 0.21 mmol) was coupled with N-(t-butyloxycarbonyl)-β-benzyl-aspartic acid (69 mg, 0.21 mmol) by the method described in Example 10a to give crude material which was flash chromatographed on silica gel eluting with a 45 to 60% gradient of EtOAc/hexanes to give, after lyophilization, the title compound (145 mg, 88%). mp 175°–184° C. $^1$H NMR (CDCl$_3$, 300 MHz) δ 0.85–1.00 (m, 18H), 1.05–2.10 (m, 24H), 1.46 (s, 9H), 2.51 (d, 1H), 2.90 (m, 2H), 3.12 (t, 1H), 3.28 (m, 1H), 4.10 (t, 1H), 4.35 (m, 4H), 5.59 (d, 1H), 6.53 (d, 1H), 6.72 (d, 1H), 6.78 (d, 1H), 7.35 (m, 5H). Anal calcd for C$_{42}$H$_{70}$N$_4$O$_9$ 0.5 H$_2$O: C, 64.36; H,9.10; N, 7.15; Found: C, 64.42; H, 8.89; N, 7.10.

MS (FAB) m/e 775 (M+H)+.

EXAMPLE 27

(2S,3R,4S)-2-(N-Acetyl-Isoleucyl-Isoleucyl-Amino)-1-cyclohexyl -3,4-dihydroxy-6-methylheptane The product of Example 24c was deprotected and converted to its free base by the method described in Example 25 to give the amino compound. To a stirred solution of the amine (56.5 mg, 0.12 mmol) in THF was added acetylimidazole (14.6 mg, 0.13 mmol). The mixture was stirred overnight at room temperature. The solvent was removed under reduced pressure and the residue dissolved in EtOAc. This solution was washed with H$_2$O and brine, dried, and concentrated in vacuo to give a residue which was flash chromatographed on silica gel to give the title compound (52.3 mg, 85%) as colorless crystals. mp 247°–248° C. $^1$H NMR (DMSO-d$_6$, 300 MHz) δ 0.83 (m, 18H), 1.00–1.80 (m, 22H), 1.83 (s, 3H), 2.92 (m, 1H), 3.08 (m, 1H), 4.10 (m, 1H), 4.20 (q, 2H), 4.50 (d, 1H), 4.71 (d, 1H), 7.52 (d, 1H), 7.82 (d, 1H), 7.91 (d, 1H). Anal calcd for C$_{28}$H$_{53}$N$_3$O$_5$ 0.25 H$_2$O: C, 65.17; H, 10.41; N, 8.14; Found: C, 64.92; H, 10.35; N, 8.00.

MS (DCI/NH$_3$) m/e 512 (M+H)+

EXAMPLE 28

2S,3R,4S)-2-(N-Boc-Cyclohexylalanyl-Isoleucyl-Amino)-1-cyclohexyl -3,4-dihydroxy-6-methylheptane The product of Example 12a was debenzylated as described in Example 12b to give the free carboxylic acid. To a stirred solution of the product of Example 24a (38.9 mg, 0.16 mmol) in anhydrous CH$_2$Cl$_2$ (3 mL) at 0° C. was added successively the carboxylic acid described above (61.4 mg, 0.16 mmol, 1 equiv), HOBT (33 mg, 0.21 mmol), and EDCI (33 mg, 0.172 mmol, 0.08 equiv). The mixture was stirred overnight allowing to warm to room temperature. The solvent was removed in vacuo and the residue taken up in EtOAc which was washed with 1N H$_3$PO$_4$ (2×), saturated NaHCO3 (2×) and saturated NaCl (2×), dried (MgSO$_4$), and concentrated in vacuo to give a residue which was flash chromatographed to give the title compound (18 mg, 29%). mp 181°–182° c. $^1$H NMR (DMSO-d$_6$, 300 MHz) δ 0.83 (m, 12H), 1.00–1.80 (m, 30H), 1.37 (2s, 9H), 2.90–3.15 (m, 3H), 3.99 (m, 1H), 4.13 (m, 1H), 4.23 (t, 1H), 4.47 (d, 1H), 4.72 (d, 1H), 6.75 (d, 1H), 6.80 (d, 1H), 7.60 (d, 2H). Anal calcd for C$_{34}$H$_{63}$N$_3$O$_6$: C, 66.96; H, 10.41; N, 6.89; Found: C, 66.91; H, 10.35; N, 6.77.

MS (DCI/NH$_3$) m/e 610 (M+H)+.

EXAMPLE 29

(2S,3R,4S)-2-(N-Boc-Isoleucyl-Isoleucyl-Amino)-1-(2-naphthyl) -3,4-dihydroxy-6-methylheptane

EXAMPLE 29A

(2S)-2 -[(tert-Butyloxycarbonyl)amino]-3-(2-naphthyl)-propanol

L-2-Naphthylalanine (1.00 g, 3.18 mmol) was protected by the method described in Example 1g to give the tert-butyloxy-carbonyl-protected compound (1.4 g, 96%).

To a stirred solution of the above acid (1.4 g, 4.4 mmol) in anhydrous THF (7 mL) at 0° C. was slowly added borane-tetrahydrofuran (BH$_3$-THF) complex (13.2 mL, 13.2 mmol, 3-fold excess). The cooling bath was removed and the mixture was allowed to warm to room temperature. After 10 min at 25° C., the mixture was again cooled to 0° C. and a solution of 1N NaOH (5 mL) was very cautiously added. The cold solution was extracted with Et$_2$O (4×) and the combined organic extracts were dried (MgSO$_4$) and concentrated in vacuo to afford the title compound (1.21 g, 90%) as colorless crystals. The 300 MHz $^1$H NMR spectrum was found to be consistent with the proposed structure.

MS (DCI/NH$_3$) m/e 302 (M+H)+.

EXAMPLE 29B

(2S,3R)-2-[(tert-Butyloxycarbonyl)amino]-1-hydroxy-6-methylheptan-4-one

To a stirred solution of anhydrous dimethyl sulfoxide (DMSO) (394 μL, 5.47 mmol, 2.2 equiv) in anhydrous CH$_2$Cl$_2$ (7 mL) at −70° C. was slowly added a 2M solution of oxalyl chloride (1.85 ml, 3.78 mmol, 1.5 equiv) at such a rate as to maintain the temperature below −65° C. After 10 minutes, a solution of the product of Example 29a (750 mg, 2.48 mmol) in 10% DMSO in CH$_2$Cl$_2$ (5 mL) was added, again keeping the temperature less than or equal to −66° C. The mixture was stirred 15 minutes, after which time dry triethylamine (1.41 mL, 9.95 mmol, 4 equiv) was slowly added to the precipitated sulfoxonium salt. After 3 minutes, anhydrous zinc iodide (183 mg, 0.49 mmol, 0.2 equiv) was added. The mixture was stirred vigorously for 5 minutes, then trimethylsilyl cyanide (TMSCN) (1.19 mL, 8.10 mmol, 3.5 equiv) was added and the mixture was allowed to warm to room temperature. After 60 minutes, the mixture was again cooled to 0° C. and a 2M solution of i-butylmagnesium chloride (13.5 mL, 27 mmol, 10.5 equiv) in ether was added maintaining the temperature equal to or lower than −0° C. The mixture was allowed to warm to room temperature and stirred for 4 hours. The mixture was poured into EtOAc containing 1:1 ice/1N H$_3$PO$_4$. The aqueous phase was extracted with EtOAc and the combined organic extracts were washed with 1N H3PO4, H$_2$O, and saturated NaCl, dried (MgSO$_4$), and concentrated in vacuo. The residue obtained was flash chromatographed on silica gel eluting with 18% EtOAc/hexane to afford the title compound (486 mg, 51%). The 300 MHz $^1$H NMR spectrum was found to be consistent with the proposed structure.

MS (DCI/NH$_3$) m/e 386 (M+H)$^+$, 403 (M+H+NH$_3$)$^+$.

EXAMPLE 29C (2 S,3R,4 S)-2-[(tert-Butyloxycarbonyl)amino]-1-(2-naphthyl) -3,4 -dihydroxy-6-methylheptane To a stirred solution of the product of Example 29b (480 mg, 1.24 mmol) in anhydrous THF (29 mL) at room temperature was added sodium borohydride (48 mg, 1.24 mmol). The mixture was stirred overnight at room temperature. The reaction mixture was concentrated in vacuo and poured into sodium chloride solution. This mixture was extracted with EtOAc, dried (MgSO$_4$), and concentrated in vacuo to give a residue which was purified by flash chromatography on silica gel eluting with 30% EtOAc/hexanes to give the title compound (249 mg, 52%). The 300 MHz $^1$H NMR spectrum was found to be consistent with the proposed structure.

MS (DCI/NH$_3$) m/e 388 (M+H)$^+$, 405 (M+H+NH$_3$)$^+$.

EXAMPLE 29D (2S,3R,4S)-2-(N-Boc-Isoleucyl-Amino)-1-(2-naphthyl)- 3,4-dihydroxy-6-methylheptane The product of Example 29c (60 mg, 0.15 mmol) was deprotected by the method described in Example 1d to give the hydrochloride salt. The salt was converted to its free base by dissolving in THF (1 mL) and adjusting the pH to 13 with 1N NaOH. The mixture was poured into CH$_2$Cl$_2$ and the aqueous phase was extracted with CH$_2$Cl$_2$. The combined organic extracts were dried over anhydrous K$_2$CO$_3$ and concentrated in vacuo to afford the free amine (45 mg, 100%).

The free amine (45 mg, 0.155 mmol) and Boc-Ile-OH hemihydrate (37 mg, 0.155 mmol) were coupled by the method described in Example 10a to give the title compound (77 mg, 99%) as colorless crystals. The 300 MHz $^1$H NMR spectrum was found to be consistent with the proposed structure.

MS (DCI/NH$_3$) m/e 501 (M+H)$^+$, 518 (M+H+NH$_3$)$^+$.

EXAMPLE 29E (2S,3R,4S)-2-(N-Boc-Isoleucyl-Isoleucyl-Amino)-1-(2- naphthyl) -3,4-dihydroxy-6-methylheptane The product of Example 29d (70 mg, 0.139 mmol) was deprotected by the method described in Example 1d and converted to its free base by the method described in Example 29d to give the free amine (56 mg, 100%).

Boc-Ile-OH hemihydrate (33.5 mg, 0.139 mmol) and the free amine (56 mg, 0.139 mmol) were coupled by the method described in Example 10a to give the title compound (85 mg, 99%) as a white solid. mp 168°-169° C. $^1$H NMR (CDCl$_3$, 300 MHz) δ 0.68-0.95 (m, 18H), 1.45 (s, 9H), 1.00-1.50 (m, 6H), 1.80 (m, 3H), 2.40 (bs, 3H), 3.00-3.42 (m, 4H), 3.82 (t, 1H), 4.16 (m, 1H), 4.40 (q, 1H), 5.23 (d, 1H), 6.91 (d, 1H), 7.20 (d, 1H), 7.40 (d, 3H), 7.65-7.80 (m, 3H). Anal calcd for C$_{35}$H$_{55}$N$_3$O$_6$: C, 68.43; H, 9.03; N, 6.85; Found: C, 68.37; H, 8.92; N, 6.79.

MS (FAB) m/e 614 (M+H)$^+$.

EXAMPLE 30

(2S ,3R,4S)-2-(N-Boc-Cyclohexylalanyl-Isoleucyl-Amino)- 1-(2-naphthyl) -3,4-dihydroxy-6-methylheptane Boc-Cha-OH (34.6 mg, 0.127 mmol) was coupled with (2S,3R,4S)-2-N-(Ile-amino)-1-(2-naphthyl)-3, 4- dihydroxy-6-methylheptane (51 mg, 0.127 mmol), obtained from the deprotection of the product of Example 29d by the method described in Example 29e, by the method described in Example 10a to give, after recrystallization from EtOAc/hexanes, the title compound (57.6 mg, 70%) as a white crystalline solid. mp 173°-174° C. $^1$H NMR (CDCl$_3$, 300 MHz) δ 0.70-1.05 (m, 12H), 1.10-1.90 (m, 19H), 1.47 (s, 9H), 3.20 (m, 1H), 3.25 (d of d, 1H), 3.48 (m, 2H), 4.00-4.20 (m, 2H), 4.55 (m, 1H), 5.78 (bd, 1H), 7.22-7.50 (m 4H), 7.70-7.83 (m, 3H). Anal calcd for C$_{38}$H$_{59}$N$_3$O$_6$: C, 69.80; H, 9.09; N, 6.43; Found: C, 69.47; H, 9.02; N, 6.38.

MS (FAB) m/e 654 (M+H)$^+$.

EXAMPLE 31

(2S,3R,4S)-2-(N-Boc-Cyclohexylalanyl-Isoleucyl- Amino)-1-(1-naphthyl) -3,4-dihydroxy-6-methylheptane The product of Example 31 was prepared in analogy to the method described in Example 30 using 1-naphthylalanine instead of 2-naphthylalanine to give the title compound. mp 149°-150° C. $^1$H NMR (CDCl$_3$+CD$_3$OD, 300 MHz) δ 0.82-1.90 (m, 31H), 1.44 (s, 9H), 3.26 (d of d, 1H), 3.38 (m, 2H), 4.05-4.23 (m, 3H), 4.62 (q, 1H), 7.30 (bd, 1H), 7.45-7.57 (m, 7H), 7.72 (m, 1H), 7.83 (d of d, 1H), 8.19 (d, 1H). Anal calcd for C$_{38}$H$59$N$_3$O$_6$ 0.5 H$_2$O: C, 68.85; H, 9.12; N, 6.34; Found: C, 69.09; H, 9.10; N, 6.31.

MS (DCI/NH$_3$) m/e 654 (M+H)$^+$, 671 (M+H+NH$_3$)$^+$.

EXAMPLE 32

N-Boc-Isoleucyl-Isoleucyl-Statyl Isopropylcarboxamide

To the product of Example 5b (50 mg, 0.1 mmol) in freshly distilled THF (5 mL) cooled to −5° C. was added NMM (11.5 μL, 0.105 mmol) followed by IBCF (13.5 μL, 0.105 mmol); the reaction mixture was stirred at −5° C. for 15 minutes. Isopropylamine (25.5 μL, 0.15 mmol) was added and the reaction mixture was allowed to warm to room temperature overnight. EtOAc with a small amount of MeOH was added and the mixture was washed with 1M H$_3$PO$_4$ (3×), saturated NaHCO$_3$ (3×), and brine, dried (Na$_2$SO$_4$), and concentrated in vacuo to give a white solid (46 mg) which was flash chromatographed on silica gel eluting with 97/3 CHCl$_3$/EtOH to give an amorphous solid. Crystallization from MeOH/H$_2$O afforded the title compound (32 mg, 59%). $^1$H NMR (CDCl$_3$, 300 MHz) δ 0.86-1.05 (m, 18H), 1.05-2.15 (m, 15H), 1.46 (2s, 9H), 2.30 (m, 2H), 2.50 (bd, 1H), 3.70 (d of t, 1N), 3.80-4.25 (m, 4H), 4.86-4.97 (m, 1H), 6.40-6.73 (m, 3H). Anal calcd for C$_{28}$H$_{54}$N$_4$O$_6$ 0.25 H$_2$O: C, 61.45; H, 10.04; N, 10.24; Found: C, 61.48; H, 9.80; N, 10.10.

MS (FAB) m/e 543 (M+H)$^+$, 565 (M+Na)$^+$.

EXAMPLE 33

[1-[N-Cbz-Isoleucyl-Isoleucyl-Amino]-3-methylbutyl (hydroxy)phosphinyl]acetic acid tert-Butyl ester

The product of Example 9 (100 mg, 0.156 mmol) and KCN 1,4,7,10,13,16-hexaoxacyclooctadecane (18-Crown-6) complex (48 mg, 0.146 mmol) were dissolved in anhydrous DMSO (5 mL) and heated at 70°–80° C. for 5 h and stirred at room temperature overnight. EtOAc was added and the mixture was washed with 1M $H_3PO_4$ and brine, dried ($Na_2SO_4$), and concentrated in vacuo to give an amorphous solid (91 mg). Flash chromatography on silica gel eluting with 90/10/1 $CHCl_3/MeOH/NH_4OH$ gave the title compound (49 mg, 67% based on a 25 mg recovery of the product of Example 9). $^1H$ NMR ($CD_3OD$, 500 MHz) δ 0.90 (m, 18H), 1.10–1.90 (m, 9H), 1.47 (2s, 9H), 2.51–2.76 (m, 2H), 4.01 (t, 1H), 4.28 (m, 2H), 5.09 (m, 2H), 7.31 (m, 5H). Anal calcd for $C_{31}H_{52}N_3O_8P$ 0.25 $NH_4OH$: C, 58.68; H, 8.46; N, 7.17; Found: C, 58.29; H, 8.44; N, 7.46.

MS (FAB) m/e 626 $(M+H)^+$, 648 $(M+Na)^+$, 670 $(M+2Na)^+$.

EXAMPLE 34

N-Boc-Isoleucyl-Isoleucyl-Statyl Isoamylcarboxamide

The product of Example 5b (50 mg, 0.1 mmol) was reacted with isoamylamine (23 μL, 0.2 mmol) by the method described in Example 32 to give a white solid (50 mg, 88%) which was flash chromatographed on silica gel eluting with 97/3 $CHCl_3/EtOH$ to give an amorphous solid. Crystallization from $MeOH/H_2O$ afforded the title compound (24 mg, 42%). $^1H$ NMR ($CDCl_3$, 300 MHz) δ 0.94 (m, 24H), 1.02–2.13 (m, 12H), 1.47 (2s, 9H), 2.23–2.57 (m, 3H), 3.25 (m, 2H), 3.71 (d of t, 1H), 3.90 (m, 2H), 4.20 (m, 1H), 4.90 (2d, 1H), 6.40–6.60 (m, 2H), 6.70 (d, 1H). Anal calcd for $C_{30}H_{58}N_4O_6$ 0.4 $H_2O$: C, 62.34; H, 10.25; N, 9.69; Found: C, 62.21; H, 9.85; N, 9.42.

MS (FAB) m/e 571 $(M+H)^+$, 471 $(M+H-Boc)^+$.

EXAMPLE 35

N-Boc-Isoleucyl-Isoleucyl-Statyl Cyclohexylmethylcarboxamide

The product of Example 5b (50 mg, 0.1 mmol) was reacted with cyclohexanemethylamine (19.5 μL, 0.15 mmol) by the method described in Example 32 to give a white solid (50 mg) which was flash chromatographed on silica gel eluting with 96.5/3.5 $CHCl_3/EtOH$ to give an amorphous solid. Crystallization from $MeOH/H_2O$ afforded the title compound (31 mg, 52%). $^1H$ NMR ($CDCl_3$, 300 MHz) δ 0.95 (m, 18H), 1.03–2.12 (m, 20H), 1.47 (2s, 9H), 2.24–2.70 (m, 3H), 3.10 (q, 2H), 3.68–4.04 (m, 3H), 4.21 (m, 1H), 4.90 (2d, 1H), 6.40–6.63 (m, 2H), 6.77 (bd, 1H). Anal calcd for $C_{32}H_{60}N_4O_6$ 0.25 $H_2O$: C, 63.91; H, 10.14; N, 9.32; Found: C, 63.80; H, 9.88; N, 9.22.

MS (FAB) m/e 597 $(M+H)^+$, 619 $(M+Na)^+$.

EXAMPLE 36

[1-[N-(N-Cbz-[(S)-2-Amino-3,3-dimethylbutanoyl])-Isoleucyl-Amino]-3-methylbutyl(hydroxy)phosphinyl]acetic acid tert-Butyl ester

EXAMPLE 36A

[1-[N-(N-Cbz-[(S)-2-Amino-3,3-dimethylbutanoyl])-Isoleucyl-Amino]-3-methylbutyl(methoxy)phosphinyl]acetic acid tert-Butyl ester

The product of Example 9c was coupled with (S)-2-(benzyloxycarbonyl)-amino-3,3-dimethylbutanoic acid by the method described in Example 1e to give the title compound. The 300 MHz $^1H$ NMR spectrum was found to be consistent with the proposed structure.

EXAMPLE 36B

[1-{N-(N-Cbz-[(S)-2-Amino-3,3-dimethylbutanoyl])-Isoleucyl-Amino]-3-methylbutyl(hydroxy)phosphinyl]acetic acid tert-Butyl ester

To the product of Example 36a (115 mg, 0.18 mmol) dissolved in anhydrous DMSO (5 mL) was added KCN:18-crown-6 (52 mg, 0.16 mmol). The reaction mixture was heated at 70°–80° C. for 3 hours, cooled to room temperature, and then partitioned between 1M $H_3PO_4$ and EtOAc. The organic phase was washed with brine, dried ($Na_2SO_4$), and concentrated under reduced pressure to afford a residue which was flash chromatographed eluting with 90/10/1 chloroform/methanol/ammonium hydroxide. The title compound was obtained as an amorphous solid (37 mg, 33%). $^1H$ NMR ($CDCl_3$, 300 MHz) δ 0.95 (m, 21H), 1.00–1.90 (m, 6H), 1.45 (s, 9H), 2.78 (m, 2H), 3.95–4.66 (m, 3H), 5.07 (bq, 2H), 5.67 (bs, 1H), 6.70 (bs, 1H), 7.30 (m, 5H), 7.55 (bs, 1H).

MS (FAB) m/e 626 $(M+H)^+$, 648 $(M+Na)^+$.

EXAMPLE 37

[1-[N-Cbz-Isoleucyl-Isoleucyl-Amino]-3-methylbutyl(hydroxy)phosphinyl]acetyl Isobutylcarboxamide

EXAMPLE 37A

[1-{N-Cbz-Isoleucyl-Isoleucyl-Amino]-3-methylbutyl(methoxy)phosphinyl]acetic Acid

The product of Example 9d (137 mg, 0.21 mmol) was dissolved in TFA (1.5 mL) and stirred at room temperature for one hour. The TFA was removed under reduced pressure and azeotroped with toluene (4×10 mL) to afford the title compound (125 mg, 100%) as a white solid. The 300 MHz $^1H$ NMR spectrum was found to be consistent with the proposed structure.

MS (FAB) m/e 584 $(M+H)^+$.

EXAMPLE 37B

[1-{N-Cbz-Isoleucyl-Isoleucyl-Amino]-3-methylbutyl(methoxy)phosphinyl]acetyl Isobutylcarboxamide

To isobutylamine (32 μL, 0.32 mmol) dissolved in $CH_2Cl_2$ and cooled to 0° C. was added the product of Example 37a (126 mg, 0.22 mmol) in $CH_2Cl_2$ followed by HOBT (36 mg, 0.26 mmol) and EDCI (46 mg, 0.24 mmol). The reaction mixture was allowed to warm to room temperature overnight and then diluted with EtOAc. Washing with 1M $H_3PO_4$ (3×), saturated NaHCO$_3$ (3×), and brine, drying (Na$_2$SO$_4$), and concentrating under reduced pressure afforded crude material (125 mg, 91%). Flash chromatography eluting with 1.75% MeOH in CHCl$_3$ afforded the title compound (78 mg, 57%). The 300 MHz $^1$H NMR spectrum was found to be consistent with the proposed structure. MS (DCI/NH$_3$) m/e 639 (M+H)$^+$, 656 (M+H+NH$_3$)$^+$.

EXAMPLE 37C

[1-[N-Cbz-Isoleucyl-Isoleucyl-Amino]-3-methylbutyl(-hydroxy)phosphinyl]acetyl Isobutylcarboxamide The product of Example 37c (75 mg, 0.12 mmol) was demethylated by the procedure described in Example 36b and purified by flash chromatography to afford the title compound as an amorphous solid (13 mg, 17%). $^1$H NMR (CD$_3$OD, 300 MHz) δ 0.80–1.00 (m, 24H), 1.05–1.90 (m, 10H), 2.70 (m, 2H), 3.04 (m, 2H), 4.00–4.28 (m, 3H), 5.09 (m, 2H), 7.33 (m, 5H).
MS (FAB) m/e 625 (M+H)$^+$, 663 (M+K)$^+$.

EXAMPLE 38

(2S,3R,4S)-2-(N-Boc-Cyclohexylalanyl-Isoleucyl-Amino)-1-(3-indolyl)-3,4-dihydroxy-6-methylheptane

EXAMPLE 38A

N-Boc-Tryptophanyl(N'-Boc) Benzyl ester

To a suspension of L-tryptophan benzyl ester hydrochloride (1.00 g, 3.02 mmol) in benzene (100 mL) was added successively 50% aqueous sodium hydroxide (10 mL), tetrabutylammonium bisulfate (100 mg) and triethylamine (1.25 mL, 8.9 mmol, 2.96 equiv) without stirring. Vigorous stirring was initiated and then di-t-butyl dicarbonate (1.97 g, 9.05 mmol, 3 equiv) was added. After stirring at room temperature for 90 minutes, water (50 mL) was added and the phases separated. The aqueous phase was extracted with benzene and the combined organic phases were washed with 10% aqueous citric acid and brine, dried (MgSO$_4$), and concentrated in vacuo. The residue obtained was flash chromatographed eluting with 15–25% gradient of EtOAc in hexanes to give the title compound (902 mg, 60%) as a white amorphous solid. The 300 MHz $^1$H NMR spectrum was found to be consistent with the proposed structure.

EXAMPLE 38B

N-Boc-Tryptophanyl(N'-Boc)-OH

To a suspension of 10% palladium on carbon (250 mg) in methanol (2 mL) was added 1,3-cyclohexadiene (200 μL, 2.02 mmol, 2 equiv). After the mixture was stirred at room temperature for 5 minutes, a solution of the product of Example 38a (500 mg, 1.01 mmol) in a 1:1 mixture of EtOAc and MeOH (2 mL) was added. After 2 hours, the catalyst was removed by filtration and the solvent removed in vacuo to afford the title compound as a white amorphous solid (334 mg, 82%). The 300 MHz $^1$H NMR spectrum was found to be consistent with the proposed structure.
MS (DCI/NH$_3$) m/e 405 (M+H)$^+$, 422 (M+H+NH$_3$)$^+$.

EXAMPLE 38C (2S,3R,4S)-2-[(tert-Butyloxycarbonyl)amino]-1-[1-N-(tert-butyloxycarbonyl)indol-3-yl]-3,4-dihydroxy-6-methylheptane The product of Example 38b was reduced using BH$_3$-THF complex by the procedure described in Example 29a to give the alcohol; the 300 MHz $^1$H NMR spectrum of which was found to be consistent with the proposed structure, MS (DCI/NH$_3$) m/e 391 (M+H)$^+$, 408 (M+H+NH$_3$)$^+$. By the procedure described in Example 29b, the alcohol was then carried on to the heptanone; the 300 MHz $^1$H NMR spectrum of which was found to be consistent with the proposed structure, MS (DCI/NH$_3$) m/e 475 (M+H)$^+$, 492 (M+H+NH$_3$)$^+$. Sodium borohydride reduction for two hours by the procedure described in Example 29c afforded the dihydroxy title compound as an amorphous solid (324 mg, 68%). The 300 MHz $^1$H NMR spectrum was found to be consistent with the proposed structure.
MS (DCI/NH$_3$) m/e 477 (M+H)$^+$, 494 (M+H+NH$_3$)$^+$.

EXAMPLE 38D (2S,3R,4S)-2-(N-Boc-Cyclohexylalanyl-Isoleucyl-Amino)-1-[1-N-(tert-butyloxycarbonyl)indol-3-yl]-3,4-dihydroxy-6-methylheptane The product of Example 38c (251 mg, 0.52 mmol) was dissolved in 4N HCl in dioxane (2 mL) and stirred at room temperature for 1 hour. The reaction mixture was concentrated in vacuo and the residue partitioned between THF-CH$_2$Cl$_2$ and 1N NaOH. The phases were separated and the aqueous layer further extracted with THF-CH$_2$Cl$_2$. The combined organic extracts were dried (K$_2$CO$_3$) and concentrated in vacuo to afford the free amine (198 mg, 100%).

The free amine (198 mg, 0.52 mmol) was coupled with Boc-Ile-OH hemihydrate (127 mg, 0.52 mmol) by the procedure described in Example 10a to give Boc-Ile-[(2S,3R,4S)-2-Amino -1-[1-(tert-butyloxycarbonyl)indol-3-yl]-3,4-dihydroxy-6-methylheptane] as an amorphous solid (75 mg, 24%); MS (DCI/NH$_3$) m/e 590 (M+H)$^+$. Deprotection and conversion to free base were performed as described above to afford the free amine (51 mg, 81%).

Boc-Cha-OH (28 mg, 0.102 mmol) was coupled with the free amine (51 mg, 0.102 mmol) by the procedure described in Example 10a to give the t it le compound (74 mg, 96%). The 300 MHz $^1$H NMR spectrum was found to be consistent with the proposed structure.
MS (FAB) m/e 643 (M+H)$^+$.

EXAMPLE 38E (2S,3R,4S)-2-(N-Boc-Cyclohexylalanyl-Isoleucyl-Amino)-1-(3-indolyl)-3,4-dihydroxy-6-methylheptane To a stirred solution of the product of Example 38d (74 mg, 99 μmol) in THF (1 mL) was added 4N NaOH (1 mL). The biphasic solution was stirred overnight at room temperature, diluted with MeOH (1 mL) to effect solution, and stirred overnight at room temperature. Concentration in vacuo afforded an aqueous residue which was extracted with CH$_2$Cl$_2$/THF (8:2). The aqueous phase was brought to neutrality with 1.1N NaHSO$_4$ and further extracted with EtOAc. The combined organic extracts were dried (MgSO$_4$) and concentrated in vacuo to afford a residue which was purified by flash chromatography and lyophilized to give the title compound (56 mg, 87%). $^1$H NMR (CDCl$_3$+CD$_3$OD, 300 MHz) δ 0.70 (m, 12H), 0.80–1.70 (m, 19H), 1.28 (s, 9H), 2.90 (d, 2H), 3.15 (m, 2H), 3.90–4.10 (m, 3H), 4.34 (m, 1H), 6.90 (m, 3H), 7.17 (d, 1H), 7.43 (d, 1H).

MS (FAB) m/e 643 (M+H)+.

EXAMPLE 39

N-Boc-Cyclohexylalanyl-Isoleucyl-Statyl Isobutylcarboxamide

The compound resulting from Example 15 (47 mg, 0.087 mmol) was reacted with isobutylamine (21 μL, 0.22 mmol) by the procedure described in Example 5c. The crude material (45 mg) was recrystallized from hot ethyl acetate and hexanes to afford the title compound (35 mg, 68%). $^1$H NMR (CDCl$_3$+CD$_3$OD 300 MHz) δ 0.86–0.97 (m, 18H), 1.46 (s, 9H), 1.10–1.98 (m, 20H), 2.29 (m, 2H), 3.05 (m, 2H), 3.91 (m, 2H), 4.12 (m, 2H). Anal calcd for C$_{32}$H$_{60}$N$_4$O$_6$: C, 64.40; H, 10.13; N, 9.39. Found: C, 64.59; H, 9.95; N, 9.07.

MS (FAB) m/e 597 (M+H)+.

EXAMPLE 40

N-Boc-Cyclohexylalanyl-Isoleucyl-Statyl N-(2-(2-Pyridyl)ethyl)Carboxamide

To the compound resulting from Example 15 (30 mg, 55.45 μmol) dissolved in tetrahydrofuran (2 mL) and cooled to 0° C. was added 1-hydroxybenzotriazole (HOBT) (9 mg, 1.2 equiv) in DMF, 4-(dimethylamino)-pyridine (DMAP) (8.1 mg, 1.2 equiv) and 1-amino-2-(2-pyridyl)ethane (16.6 μL, 2.5 equiv). After the mixture became homogeneous, EDCI (12.8 g, 1.2 equiv) was added. After stirring at room temperature for 3 days, the reaction mixture was concentrated at reduced pressure. The residue obtained was purified by preparative HPLC and lyophilized to give the title product (32.4 mg, 91%). $^1$H NMR (CDCl$_3$, 300 MHz) δ 0.87–1.00 (m, 12H), 1.46 (s, 9H), 1.20–1.82 (m, 19H), 2.04 (bs, 1H), 2.27 (m, 1H), 2.38 (m, 1H), 3.41 (m, 2H), 3.86 (m, 2H), 4.13 (m, 2H), 5.22 (m, 1H), 7.10 (m, 1H), 7.60–7.80 (m, 2H), 7.85 (d, 1H), 8.32 (bt, 1H), 8.70 (m, 1H). Anal calcd for C$_{35}$H$_{59}$N$_5$O$_6$·1.25 TFA: C, 56.99; H, 7.67; N, 8.87. Found: C, 57.13; H, 7.70; N, 8.88.

MS (DCI/NH$_3$) m/e 646 (M+H)+.

EXAMPLE 41

N-Boc-Cyclohexylalanyl-Isoleucyl-Statyl N-(2-N',N'-Dimethylaminoethyl)Carboxamide To the compound resulting from Example 15 (30 mg, 55.45 μmol) was reacted with N,N-dimethylethylenediamine (15 μL, 2.5 equiv) by the procedure described in Example 40. Purification by preparative HPLC and lyophilization afforded the title compound (31.8 mg, 94%). $^1$H NMR (CDCl$_3$, 300 MHz) δ 0.85–1.00 (m, 18H), 1.45 (s, 9H), 1.00–1.80 (m, 19H), 2.25 (m, 1H), 2.45 (m, 1H), 3.01 (d, 2H), 3.22 (m, 1H), 3.50 (m, 1H), 3.93–4.20 (m, 4H), 5.59 (m, 1H), 7.40 (m, 1H), 8.03 (bd, 1H), 8.45 (m, 1H), 9.63 (m, 1H). Anal calcd for C$_{32}$H$_{61}$N$_5$O$_6$·1.1 TFA: C, 55.97; H., 8.46; N, 9.29. Found: C, 55.71; H, 8.49; N, 9.50.

MS (DCI/NH$_3$) m/e 612 (M+H)+.

EXAMPLE 42

N-Boc-Cyclohexylalanyl-Isoleucyl-Statyl N-(2-(Morpholin-4-yl)ethyl)Carboxamide The compound resulting from Example 15 (30 mg, 55.45 μmol) was reacted with N-(2-aminoethyl)morpholine (18 μL, 2.5 equiv) by the procedure described in Example 40. Purification by preparative HPLC and lyophilization afforded the title product (24 mg, 66%). $^1$H NMR (CDCl$_3$, 300 MHz) δ 0.84–1.00 (m, 12H), 1.45 (s, 9H), 1.00–1.77 (m, 19H), 2.20–2.47 (m, 2H), 2.40–3.05 (m, 7H), 3.20 (bd, 1H), 3.53 (bt, 1H), 3.85–4.28 (m, 7H), 5.60 (bd, 1H), 7.50 (bs, 1H), 8.20 (bd, 1H), 8.7 (m, 1H). Anal calcd for C$_{34}$H$_{61}$N$_5$O$_7$·1.3 TFA: C, 55.36; H, 8.06; N, 8.35. Found: C, 55.16; H, 8.14; N, 8.38.

MS (DCI/NH$_3$) m/e (M+H)+.

EXAMPLE 43

(2S,3R,4S)-2-{[IN-(4-Methylpiperazin-1-yl-carbonyl)-Cyclohexylalanyl-Isoleucyl]amino}-1-(2-naphthyl)-3,4-dihydroxy-6-methylheptane Hydrochloride

EXAMPLE 43A

N-(4-Methylpiperazin-1-yl-carbonyl)-Cyclohexylalanine

To Cyclohexylalanine methyl ester hydrochloride salt (1.00 g, 4.51 mmol) suspended in toluene (25 mL) was added bis (trichloromethyl) carbonate (triphosgene) (669.2 mg, 0.5 equiv). The reaction mixture was warmed at 100° C. for 3 hours and then concentrated under reduced pressure to afford a semi-solid residue. To this residue dissolved in methylene chloride (15 mL) and cooled to 0° C. was added N-methylpiperazine (0.50 mL, 1.0 equiv). After stirring for 1 hour, the reaction mixture was concentrated at reduced pressure to afford a semi-solid residue. Flash chromatography on silica gel eluting with 4% methanol in chloroform afforded the title product (629 mg, 45%).

To the methyl ester (629 mg, 2.022 mmol) dissolved in tetrahydrofuran (16 mL) and water (2 mL) and cooled to 0° C. was added lithium hydroxide monohydrate (169.7 mg, 2.0 equiv) in water (2 mL). After 90 minutes, the tetrahydrofuran was removed under reduced pressure and the aqueous solution acidified to pH 3 by the careful addition of 1N HCl. This solution was placed on a column of Dowex 1-X8 and 50W-X8 made acidic by packing and equilibrating with 1N HCl. The column was eluted with 0.1N HCl and 1.0N HCl. The title product was obtained as an amorphous solid. MS (DCI/NH$_3$) m/e 298 (M+H)+. The 300 MHz $^1$H NMR spectrum was found to be consistent with the proposed structure.

EXAMPLE 43B

(2S,3R,4S)-2-{[N-(4-Methylpiperazin-1-yl-carbonyl)-Cyclohexylalanyl-Isoleucyl]amino }-1-(2-naphthyl)-3,4-dihydroxy-6-methylheptane Hydrochloride The compound resulting from Example 29d (27.8 mg, 55.5 μmol) was deprotected as described in Example 1d to afford (2S,3R,4S)-2-N-(Isoleucyl-amino)-1-(2-naphthyl)-3,4-dihydroxy-6-methylheptane.

The compound resulting from Example 43a (18.1 mg, 61 μmol) was coupled with the above amine (22.2 mg, 0.91 equiv) using the procedure described in Example 1e to afford crude product (31 mg, 76%). Flash chromatography on silica gel eluting with 20% methanol in methylene chloride afforded pure material.

The free amine was taken up in 4N HCl in dioxane (1.5 mL) and then concentrated at reduced pressure to afford the hydrochloride salt. $^1$H NMR (DMSO-d$_6$, 300 MHz) δ 0.62–0.89 (m, 12H), 0.90–1.80 (m, 19H), 2.23 (m, 3H), 2.90–3.20 (m, 4H), 3.30 (s, 3H), 3.40–3.74 (m, 3H), 4.18 (m, 1H), 4.32 (m, 1H), 5.00 (d, 0.5H), 6.55 (d, 0.5H), 7.40–7.57 (m, 4H), 7.70–7.88 (m, 4H). Anal calcd

EXAMPLE 44

N-Boc-tert-Butylalanyl-Isoleucyl-Statyl-OEt tert-Butylalanine (250 mg, 1.7 mmol) was protected by the procedure described in Example 1g. The 300 MHz $^1$H NMR spectrum was found to be consistent with the proposed structure. MS (DCI/NH$_3$) m/e 246 (M+H)$^+$, 263 (M+H+NH$_3$)$^+$.

The free base of Example if (69 mg, 0.22 mmol) was coupled with the above carboxylic acid (53 mg, 0.22 mmol) by the procedure described in Example 3c. The product was recrystallized from ethyl acetate and hexanes to afford the title compound (108 mg, 92%). $^1$H NMR (CDCl$_3$, 300 MHz) δ 0.86–0.99 (m, 21H), 1.27 (d of t, 3H), 1.46 (s, 9H), 1.00–2.07 (m, 8H), 2.47 (m, 2H), 3.40 (d of d, 1H), 3.97–4.27 (m, 6H), 4.85 (m, 1H), 6.32 (m, 1H), 6.60 (m, 1H). Anal calcd for C$_{28}$H$_{53}$N$_3$O$_7$: C, 61.85; H, 9.82; N, 7.73. Found: C, 62.05; H, 10.01; N. 7.52.

MS (FAB) m/e 544 (M+H)$^+$.

EXAMPLE 45

N-Boc-tert-Butylalanyl-Isoleucyl-Statyl-OH

The compound resulting from Example 44 (40 mg, 74 μmol) was hydrolyzed by the procedure described in Example 2 to give, after recrystallization from methylene chloride and hexanes, the title product (35 mg, 92%). $^1$H NMR (CDCl$_3$, 300 MHz) δ 0.85–1.00 (m, 21H), 1.46 (s, 9H), 1.03–2.03 (m 8H), 2.53 (t, 2H), 3.07–4.30 (m, 4H), 5.00 (bd, 1H), 6.82 (bd, 1H). Anal calcd for C$_{26}$H$_{49}$N$_3$O$_7$·1.0 H$_2$O: C, 58.51; H, 9.63; N. 7.87. Found: C, 58.65; H, 9.66; N, 7.89.

MS (FAB) m/e 516 (M+H)$^+$, 538 (M+Na)$^+$.

EXAMPLE 46

(2S,3R,4S)-2-{[N-Boc-Aspartyl(β-O-Benzyl)-Isoleucyl-Isoleucyl]amino}-1-(2-naphthyl)-3,4-dihydroxy-6-methylheptane The compound resulting from Example 29 was deprotected by the procedure described in Example 1d to give (2S,3R,4S)-2-N-(Isoleucyl-Isoleucyl-amino)-1-(2-naphthyl) -3,4-dihydroxy-6-methylheptane]. This amine (41 mg, 0.079 mmol) was coupled with Boc-Aspartic(β-OBenzyl) acid (25.3 mg, 0.079 mmol) by the procedure described in Example 10a to give crude product. Recrystallization from ethyl acetate and hexanes afforded the title compound (51 mg, 80%) as colorless crystals. m.p. 178°–179° C. $^1$H NMR (CDCl$_3$, 300 MHz) δ 0.58 (m, 6H), 0.94 (m, 12H), 1.48 (s, 9H), 1.00–2.08 (m, 9H), 2.65 (bs, 1H), 2.90–3.43 (m, 6H), 4.07–4.23 (m, 3H), 4.40 (d of d, 1H), 4.67 (d of d, 1H), 5.11 (d of d, 2H), 5.62 (d, 1H), 6.67 (d of d, 1H), 6.80 (d, 1H), 7.29–7.43 (m, 7H), 7.64–7.78 (m, 4H). Anal calcd for C, 67.46; H, 8.12; N, 6.84. Found: C, 67.24; H, 7.95; N, 6.59.

MS (FAB) m/e 819 (M+H)$^+$.

EXAMPLE 47

N-Boc-Isoleucyl-Isoleucyl-Statyl N-(2-(2-Pyridyl)ethyl)Carboxamide

The compound resulting from Example 10e (48 mg, 95.8 μmol) was reacted with 2-(2-aminoethyl)pyridine (29 μL, 2.5 equiv) by the procedure described in Example 40. Purification by HPLC followed by lyophilization afforded the title product. $^1$H NMR (CDCl$_3$, 300 MHz) δ 0.87–1.00 (m 18H), 1.46 (s, 9H), 1.00–2.07 (m, 9H), 2.28 (m, 2H), 3.32 (t, 2H), 3.60–3.96 (m, 6H), 4.14 (t, 1H), 5.28 (bd, 1H), 6.92 (m, 1H), 7.50–7.82 (m, 3H), 8.24 (t, 1H), 8.77 (bd, 1H). Anal calcd for C$_{32}$H$_{55}$N$_5$O$_6$·1.65 TFA: C, 53.40; H, 7.19; N, 8.82. Found: C. 53.07; H, 7.10; N, 9.25.

MS (FAB) m/e 606 (M+H)$^+$.

EXAMPLE 48

(2S,3R,4S)-2-{[N-Succinyl-Cyclohexylalanyl-Isoleucyl]amino}-1-(2-naphthyl)-3,4-dihydroxy-6-methylheptane The compound resulting from Example 30 (250 mg, 0.38 mmol) was deprotected by the procedure described in Example 1d. This amine hydrochloride was reacted with succinic anhydride (7 mg, 1.05 equiv) by the procedure described in Example 19. Purification by MPLC eluting with 10% methanol in methylene chloride containing 1% ammonium hydroxide and lyophilization afforded the title compound. m.p. 156°–160° C. $^1$H NMR (DMSO-d$_6$, 300 MHz) δ 0.60–0.87 (m, 12H), 0.88–1.80 (m, 19H), 2.25–2.47 (m, 4H), 2.90–3.20 (m, 4H), 3.32 (d, 1H), 4.15 (t, 1H), 4.33 (m, 2H), 5.03 (bd, 1H), 7.45 (m, 3H), 7.64–7.89 (m, 5H), 8.04 (bd, 1H). Anal calcd for C$_{37}$H$_{55}$N$_3$O$_7$·H$_2$O: C, 66.14; H, 8.55; N, 6.25. Found: C, 65.76; H, 8.61; N. 6.33.

MS (FAB) m/e 654 (M+H)$^+$.

EXAMPLE 49

(2S,3R,4S)-2-{[N-Boc-Cyclohexylalanyl-Isoleucyl-]amino}-1-(4-tert-butylphenyl) -3,4-dihydroxy-6-methylheptane

EXAMPLE 49A tert-Butyl 3-(4-tert-Butyl)phenylpropionate

To a stirred solution of anhydrous isopropylcyclohexylamine (5.18 mL, 31.5 mmol, 1.05 equiv) in anhydrous tetrahydrofuran (30 mL) at 0° C. was added n-butyllithium (13.0 mL, 30.3 mmol, 1.01 equiv). The resultant solution was cooled to −75° C. and anhydrous tert-butyl acetate (4.04 mL, 30 mmol) was added at a rate such that the temperature did not exceed −73° C. The enolate solution was stirred for 1 hour and then 1,3-dimethyl,3,4,5,6-tetrahydro-2(1H)-pyrimidinone (DMPU) (3.80 mL, 30 mmol, 1 equiv) followed by a precooled solution of freshly distilled 4-tert-butylbenzyl bromide (5.51 mL, 30 mmol, 1 equiv) in tetrahydrofuran (5 mL) was added at rate such that the temperature remained below −65° C. The cooling bath was removed and the mixture warmed to room temperature and poured into 1.1M sodium bisulfate and ether. The phases were separated and the organic phase washed with solutions of sodium bicarbonate and sodium chloride (2×), dried (magnesium sulfate) and concentrated in vacuo to afford crude material. Flash chromatography on silica gel eluting with 5% ether in hexanes gave the title compound (7.247 g, 92%) as a colorless oil.

EXAMPLE 49B tert-Butyl 3-(4-tert-Butyl)phenylpropionic Acid

To a stirred solution of the compound resulting from Example 49a (7.24 g, 27.6 mmol) in anhydrous methylene chloride (8 mL) at 0° C. was added TFA (4 mL, 52 mmol, 1.9 equiv). The cooling bath was removed and the mixture stirred overnight at room temperature. The volatiles were moved in vacuo to afford a white crystalline solid. The product obtained was dissolved in 3N sodium hydroxide (60 mL) and washed with hexane (2×). The aqueous layer was cooled to 10° C. and the pH adjusted to 1.0 by the careful additon of 3N HCl (70 mL). The precipitated acid was extracted with ether (2×50 mL); the combined organic extracts were dried over magnesium sulfate and concentrated a in vacuo to afford the title compound (5.14 g, 90%).

EXAMPLE 49C (4S)-3-{3-(4-tert-Butylphenyl)-1-oxopropyl}-4-(phenyl-methyl)-2-oxazolidone To a stirred solution of the compound resulting from Example 49b (3.00 g, 14.54 mmol) in anhydrous tetrahydrofuran (100 mL) at −78° C. was added successively anhydrous triethylamine (2.63 mL, 18.9 mmol, 1.3 equiv) and freshly distilled pivaloyl chloride (2 mL, 15.99 mmol, 1.1 equiv). The reaction mixture was stirred at −78° C. for 15 minutes, 0° C. for 45 minutes, and then re-cooled to −78° C.

In a separate flask, n-butyllithium (2.22M solution in hexanes) (6.9 mL, 15.3 mmol, 1.05 equiv) was added to a stirred solution of the oxazolidinone (2.83 g, 15.99 mmol, 1.1 equiv) in anhydrous tetrahydrofuran (35 mL) at −78° C. at a rate such that the temperature did not exceed −72° C. The cold oxazolidinide solution was transferred via cannula into the mixed anhydride solution, and the reaction mixture was stirred overnight allowing to gradually warm to room temperature. The reaction was quenched by the addition of 1N sodium hydrogen sulfate (120 mL), and most of the tetrahydrofuran was removed in vacuo. The resulting aqueous mixture was extracted with methylene chloride (3×50 mL) and the combined organic extracts washed with solutions of sodium bicarbonate and sodium chloride, dried over sodium sulfate, and concentrated in vacuo. The residue obtained was flash chromatographed on silica gel eluting with 10% ethyl acetate in hexanes to afford the title product (5.31 g, 76%). The 300 MHz $^1$H NMR spectrum was found to be consistent with the proposed structure.

EXAMPLE 49D (3(2S),4S)-3-{2-Azido-3-(tert-butylphenyl)-1-oxopropyl}-4-(phenylmethyl)-2-oxazolidinone To anyhydrous tetrahydrofuran (27 mL) at −78° C. was added a solution of potassium hexamethyldisilazide (18.96 mL, 9.48 mmol, 1.1 equiv) followed by a solution of the compound resulting from Example 49c (3.10 g, 8.66 mmol) at −78° C. in anhydrous tetrahydrofuran (41 mL) such that the temperature did not exceed −75° C. After 30 minutes, a pre-cooled solution of 2,4,6-triisopropylbenzenesulfonyl azide (Trysl azide) (3.37 g, 10.92 mmol, 1.2 equiv) in anhydrous tetrahydrofuran (29 mL) was added rapidly through a wide bore cannula. The mixture was stirred for 1 minute upon completion of the addition, and then acetic acid (2.27 mL, 39.8 mmol, 4.6 equiv) was added in one portion. The cooling bath was removed and replaced with a water bath at 40° C. allowing the reaction temperature to quickly rise to 32° C. After 30 minutes at this temperature, the mixture was poured into brine and extracted with methylene chloride (2×). The combined organic extracts were washed with sodium bicarbonate solution, dried over magnesium sulfate, and concentrated in vacuo to afford crude material. Purification by flash chromatography on silica gel eluting with 50% methylene chloride in hexanes afforded partially purified material which was rechromatographed eluting with a 45% to 100% gradient of methylene chloride in hexanes to afford the title compound ( 2.09 g, 59 % ).

EXAMPLE 49E (2S)-2-Azido-3-(4-tert-Butylphenyl)propionic acid

To the compound resulting from Example 49d (2.09 g, 5.14 mmol) dissolved in tetrahydrofuran (38 mL) and water (12.8 mL) and cooled to 0° C. was added lithium hydroxide monohydrate ( 430 mg, 10.2 mmol, 2.0 equiv). After 30 minutes, the mixture was poured into 0.5N sodium bicarbonate (60 mL) and concentrated at reduced pressure to remove the tetrahydrofuran. The aqueous solution was extracted with methylene chloride (4×) and then adjusted to pH 1.0 by the careful addition of 3N sulfuric acid and extracted with ether (4×). The combined ether extracts were dried over magnesium sulfate and concentrated in vacuo to afford the title compound ( 1.27 g, 99%) as colorless crystals.

EXAMPLE 49F (2S)-2-Boc-Amino-3-(4-tert-Butylphenyl)propan-1-ol

To a stirred suspension of lithium aluminum hydride (748 mg, 19.7 mmol, 4 equiv) in anhydrous tetrahydrofuran (50 mL) at 0° C. was added a solution of the compound resulting from Example 49e (1.22 g, 4.93 mmol) in tetrahydrofuran (5 mL). The cooling bath was removed and the mixture warmed to room temperature. After 30 minutes, the mixture was heated under reflux for 2 hours. After cooling to room temperature, 4N sodium hydroxide was cautiously added. The solvent was removed in vacuo and the residue obtained extracted with methylene chloride (3×). The combined organic extracts were dried over anhydrous potassium carbonate and concentrated in vacuo to afford the amino compound (883 mg, 86%).

The amino compound (836 mg, 4.03 mmol) was protected using the procedure described in Example 1g to afford crude material. Flash chromatography on silica gel eluting with with 40% ethyl acetate in hexanes afforded the title compound (957 mg, 77%). The 300 MHz $^1$H NMR spectrum was found to be consistent with the proposed structure.

EXAMPLE 49G (2S,3R,4S)-2-Amino-1-(4-tert-butylphenyl)-3,4-dihydroxy-6-methylheptane The compound resulting from Example 49f (235 mg, 0.77 mmol) was treated in analogy to the procedure described in the literature-for the 1-cyclohexyl compound: Luly, J. R.; Hsiao, C. N.; BaMaung, N.; Plattner, J. J. J. Org. Chem. 1988, 53, 6109. This compound (58 mg, 0.147 mmol) was deprotected by the procedure described in Example 1d to give the hydrochloride salt. The salt was partitioned between methylene chloride and 1N sodium hydroxide. The aqueous layer was further extracted with methylene chloride and the combined organic extracts were dried over anhydrous potassium carbonate and concentrated in vacuo to afford the title compound (43.2 mg, 100%) as colorless crystals.

EXAMPLE 49H (2S,3R,4S)-2-{[H-Isoleucyl]amino}-1-(4-tert-butylphenyl)-3,4-dihydroxy-6-methylheptane The compound resulting from Example 49g (43.2 mg, 0.147 mmol) was coupled with Boc-Ile-OH hemihydrate (35.4 mg, 0.147 mmol) by the procedure described in Example 10a to give the title compound as a white crystalline solid (74.7 mg, 100%).

The protecting group was removed using the procedure described in Example 1d to give the hydrochloride salt. The salt was treated as described in Example 49g to give the title compound (59.9 mg, 100%) as colorless crystals.

EXAMPLE 49I (2S,3R,4S)-2-([N-Boc-Cyclohexylalanyl-Isoleucyl-]amino}-1-(4-tert-butylphenyl)-3,4-dihydroxy-6-methylheptane The compound resulting from Example 49h (59.9 mg, 0.147 mmol) was coupled with Boc-Cha-OH (40.7 mg, 0.147 mmol) by the procedure described in Example 10a to give the title compound (94.3 mg, 97%) as white solid, which was recrystallized from ethyl acetate and hexanes. m.p. 171°–172° C. $^1$H NMR (CDCl$_3$, 300 MHz) δ 0.78–0.95 (m, 12H), 1.29 (s, 9H), 1.47 (s, 9H), 0.95–2.20 (m, 19H), 2.94 (m, 2H), 3.19–3.45 (m, 2H), 4.00 (m, 1H), 4.17 (m, 1H), 4.60 (d of d, 1H), 4.86 (bd, 1H), 6.43 (d, 1H), 6.69 (bd, 1H), 7.22 (d of d, 2H). Anal calcd for C$_{38}$H$_{65}$N$_3$O$_6$: C, 69.16; H, 9.93; N, 6.37. Found: C, 69.66; H, 9.95; N, 6.07.

MS (FAB) m/e 660 (M+H)$^+$.

EXAMPLE 50

(2S,3R,4S)-2-{[N-Acetyl-Cyclohexylalanyl-Isoleucyl-]amino}-1-(4-tert-butylphenyl)-3,4-dihydroxy-6-methylheptane The compound resulting from Example 49 (30.7 mg, 46 μmol) was deprotected by the procedure described in Example 1d to give the hydrochloride salt. The salt was treated as described in Example 49g to give the free amine (26 mg, 100%) as a white solid.

The free amine (26 mg, 46 μmol) was reacted with acetyl imidazole (5.5 mg, 49 μmol) by the procedure described in Example 27 to give the N-acetyl compound. Flash chromatography on silica gel eluting with 85% ethyl acetate in hexanes afforded the title compound (18.7 mg, 67%). m.p. 199°–201° C. $^1$H NMR (DMSO-d$_6$, 300 MHz) δ 0.64–0.90 (m, 12H), 1.26 (s, 9H), 0.90–1.80 (m, 19H), 1.83 (s, 3H), 2.74 (m, 1H), 3.05 (m, 2H), 3.05 (m, 2H), 3.32 (d, 1H), 4.10–4.40 (m, 4H), 4.97 (d, 1H), 7.22 (d of d, 4H), 7.60 (d, 1H), 7.77 (d, 1H), 8.03 (d, 1H). Anal calcd for C$_{35}$H$_{59}$N$_3$O$_5$: C, 69.85; H, 9.88; N, 6.98. Found: C, 70.03; H, 9.62; N, 6.19.

MS (FAB) m/e 602 (M+H)$^+$.

EXAMPLE 51

(2S,3R,4S)-2-{[N-Acetyl-Cyclohexylalanyl-Isoleucyl-]amino}-1-(2-naphthyl)-3,4-dihydroxy-6-methylheptane The compound resulting from Example 30 (33 mg, 50 μmol) was deprotected using the procedure described in Example 1d and converted to its free base by the procedure described in Example 49g to give the free amine.

The amine (27.9 mg, 0.050 mmol) was acetylated using acetyl imidazole (6.0 mg, 0.054 mmol, 1.08 equiv) using the procedure described in Example 27. Flash chromatography on silica gel eluting with ethyl acetate afforded the title product (25.7 mg, 85%). m.p. 192°–194° C. $^1$H NMR (DMSO-d$_6$, 300 MHz) δ 0.60–0.87 (m, 12H), 0.88–1.80 (m, 19H), 1.83 (s, 3H), 2.92–3.20 (m, 4H), 4.16 (m, 1H), 4.32 (d of d, 3H), 5.07 (d, 1H), 7.45 (m, 3H), 7.64–7.88 (m, 6H), 8.01 (d, 1H). Anal calcd for C$_{35}$H$_{53}$N$_3$O$_5$: C, 70.56; H, 8.97; N, 7.05. Found: C, 71.34; H, 8.81; N, 6.53.

MS (FAB) m/e 596 (M+H)$^+$.

EXAMPLE 52

N-Boc-Isoleucyl-Isoleucyl-Statyl N-Methyl-N-Isobutyl Carboxamide

To the compound resulting from Example 5b (37 mg, 0.074 mmol) was reacted with N-methyl-N-isobutylamine (8.8 μL, 0.074 mmol) by the procedure described in Example 3c to afford crude product (29 mg). Flash chromatography on silica gel eluting with 3% ethanol in chloroform afforded the title product (16 mg, 38%). $^1$H NMR (CDCl$_3$, 300 MHz) δ 0.75–0.88 (m, 24H), 1.47 (s, 9H), 0.90–2.00 (m, 12H), 2.32 (m, 2H), 2.85 (m, 2H), 3.10 (m, 2H), 3.81 (m, 3H), 4.18 (m, 1H), 4.73 (m, 1H), 6.77 (m, 1H), 7.43–7.72 (m, 2H). Anal calcd for C$_{30}$H$_{58}$N$_4$O$_6$·0.5 H$_2$O: C, 62.15; H, 10.26; N, 9.66. Found: C, 61.95; H, 9.79; N, 9.35.

MS (FAB) m/e 571 (M+H)$^+$.

EXAMPLE 53

(2S,3R,4S)-2-{[N-(Morpholin-1-yl-carbonyl)-Cyclohexylalanyl-Isoleucyl]amino}-1-(2-naphthyl)-3,4-dihydroxy-6-methylheptane

EXAMPLE 53A

N-(Morpholin-1-yl-carbonyl)-Cyclohexylalanine

To Cyclohexylalanine methyl ester hydrochloride salt (200 mg, 0.902 mmol) suspended in toluene (5 mL) under nitrogen was added triphosgene (133.8 mg, 0.5 equiv). The reaction mixture was warmed at 100° C. for 2 hours and then concentrated at reduced pressure. The residue obtained was taken up in methylene chloride (3 mL), cooled to 0° C., and treated with morpholine (79 μL, equiv). After 10 minutes at 0° C. the reaction mixture was concentrated at reduced pressure to afford the methyl ester as a semi-solid residue.

MS (DCI/NH$_3$) m/e 2 99 (M+H)$^+$.

The methyl ester (269 mg, 0.902 mmol) was hydrolyzed with lithium hydroxide by the procedure described in Example 43a to afford the title compound (234 mg, 91%).

EXAMPLE 53B (2S,3R,4S)-2-{[N-(Morpholin-1-yl-carbonyl)-Cyclohexylalanyl-Isoleucyl]amino}-1-(2-naphthyl)-3,4-dihydroxy-6-methylheptane To the compound resulting from Example 53a (19.5 mg, 68.75 μmol) was coupled with the free amine (25 mg, 0.91 equiv) of Example 29d, which had been deprotected by the procedure described in Example 1d and converted to its free base by the procedure described in Example 49g, by the procedure described in Example 1e to afford crude material (36.5 mg, 88%). Flash chromatography on silica gel eluting with 1:1 ethyl acetate/hexanes to afford the title compound (22.7 mg, 50%). $^1$H NMR (DMSO-d$_6$, 300 MHz) δ 0.63–0.87 (m, 12H), 0.90–1.75 (m, 19H), 2.90–3.20 (m, 3H), 3.30 (m, 2H), 3.53 (m, 2H), 4.18 (m, 1H), 4.32 (m, 1H), 5.02

(d, 0.5H), 6.50 (d, 0.5H), 7.45 (m, 1.5H), 7.60 (d, 0.5H), 7.71–7.87 (m, 2.5H). Anal calcd for $C_{38}H_{58}N_4O_6 \cdot H_2O$: C, 66.64; H, 8.83; N, 8.18.
Found: C, 66.69; H, 8.47; N, 8.06.
MS (FAB) m/e 667 (M+H)+.

EXAMPLE 54

(2S,3R,4S)-2-{[{N-(N,N-Dimethylaminoethyl)-N-methylamino}carbonyl
-Cyclohexylalanyl-Isoleucyl]amino}-1-(2-naphthyl)-3,4-dihydroxy-6-methylheptane

EXAMPLE 54A

}N-(N,N-Dimethylaminoethyl)-N-methylamino}carbonyl-Cyclohexylalanine

To Cyclohexylalanine methyl ester hydrochloride (1.00 g, 4.51 mmol) suspended in toluene (25 mL) and warmed to 100° C. under nitrogen was added triphosgene (669 mg, 0.5 equiv). After 3.5 hours, the reaction mixture was concentrated at reduced pressure. The residue obtained was dissolved in methylene chloride and cooled to 0° C. N,N-dimethyl-N'-methylethylenediamine (0.51 mL, 1.0 equiv) was added, and the reaction mixture was allowed to stir for 1 hour. The solvents were removed under reduced pressure to afford crude product. Flash chromatography on silica gel eluting with 1–10% methanol in chloroform gave the methyl ester (1.016 g, 72%).

The methy ester (1.016 g, 3.246 mmol) was hydrolyzed with lithium hydroxide (272 mg, 2 equiv) by the procedure described in Example 43a. Ion exchange chromatography eluting with 0.1N hydrochloric acid afforded the title compound as a white amorphous solid (710 mg, 73%).

EXAMPLE 54B (2S,3R,4S)-2-{[{N-(N,N-Dimethylaminoethyl)-N-methylamino}carbonyl-Cyclohexylalanyl
-Isoleucyl]amino}-1-(2-naphthyl)3,4-dihydroxy-6-methylheptane To the compound resulting from Example 54a (20.6 mg, 68.75 μmol) was coupled with the free base of Example 29d (25 mg, 0.91 equiv), which had been deprotected by the procedure described in Example 1d and converted to its free base by the procedure described in Example 49g, by the procedure described in Example 1e to give crude material. Flash chromatography on silica gel eluting with 2% methanol in chloroform followed by preparative HPLC followed by lyophilization afforded the title compound. $^1H$ NMR (DMSO-d$_6$, 300 MHz) δ 0.67–0.86 (m, 12H), 0.90–1.80 (m, 19H), 2.78 (m, 5H), 2.90–3.25 (m, 8H), 3.54 (m, 2H), 4.15–4.38 (m, 2H), 5.07 (d, 1H), 6.43 (d, 1H), 7.45 (m, 2H), 7.64–7.90 (m, 6H). Anal calcd for $C_{39}H_{63}N_5O_5 \cdot 1.7$ TFA: C, 58.15; H, 7.45; N, 8.00. Found: C, 58.22; H, 7.58; N, 7.96.
MS (FAB) m/e 682 (M+H)+.

EXAMPLE 55

(2S,3R,4S)-2-{[N-(4-Methylpiperazin-1-yl-sulfonyl)-Cyclohexylalanyl-Isoleucyl]amino}-1-(2-naphthyl)-3,4-dihydroxy-6-methylheptane

EXAMPLE 55A

N-(4-Methylpiperazin-1-yl-sulfonyl)-Cyclohexylalanine

To a solution of N-methylpiperazine (1.48 mL, 13.3 mmol) in dioxane (6.7 mL) cooled to 0° C. was added 4N hydrochloric acid in dioxane (10 mL). The reaction was very exothermic, and the mixture was stirred until the reaction cooled to room temperature. The solvent was removed under reduced pressure and chased with ether (2×). The solid obtained was taken up in acetonitrile (7 mL) and sulfuryl chloride (3.53 mL, 3.3 equiv) was added. The mixture was warmed at reflux for 24 hours and the product removed by filtration and washed with 1:1 acetonitrile/ether (100 mL). This crude material was recrystallized from hot methanol and acetonitrile to afford 4-methylpiperazin-1-ylsulfonyl chloride (1.36 g, 44%) as a white crystalline solid.

To Cyclohexylalanine methyl ester hydrochloride salt (1.00 g, 4.51 mmol) suspended in methylene chloride (6 mL) was added the above sulfonyl chloride (893 mg, 1.0 equiv) and triethylamine (2.01 mL, 3.2 equiv). The reaction mixture was stirred overnight at room temperature. The solvents were removed under reduced pressure, and the residue obtained was purified by flash chromatography on silica gel eluting with ethyl acetate to afford the methyl ester (409 mg, 29%).
MS (DCI/NH$_3$) m/e 348 (M+H)+.

The methyl ester (409 mg, 1.174 mmol) was hydrolyzed with lithium hydroxide (109 mg) by the procedure described in Example 43a to afford crude material which was purified by ion exchange chromatography to afford the title compound (341 mg, 87%).

EXAMPLE 55B (2S,3R,4S)-2-{[N-(4-Methylpiperazin-1-yl-sulfonyl)-Cyclohexylalanyl-Isoleucyl]amino}-1-(2-naphthyl)-3,4-dihydroxy-6-methylheptane To the compound resulting from Example 55a (22.9 mg, 68.75 μmol) was coupled with Example 29d (25 mg, 0.91 equiv), which had been converted to its hydrochloride salt by the procedure described in Example 1d and then converted to its free base by the procedure described in Example 49g, by the procedure described in Example 1e to afford crude product (25.4 mg, 57%). Preparative HPLC afforded the title product. $^1H$ NMR (DMSO-d$_6$, 300 MHz) δ 0.70–0.87 (m, 12H), 0.95–1.80 (m, 19H), 2.27–2.70 (m, 2H), 2.75–3.20 (m, 11H), 3.50–3.94 (m, 5H), 4.20–4.40 (m, 3H), 5.15 (bd, 1H), 7.40–8.03 (m, 11H), 9.83 (bs, 1H). Anal calcd for $C_{38}H_{61}N_5O_6 \cdot 1.55$ TFA: C, 55.30; H, 7.06; N, 7.84. Found: C, 55.27; H, 7.07; N, 7.65.
MS (FAB) m/e 716 (M+H)+.

Isolation and Characterization of Endothelin Converting Enzyme

Rat lung plasma membranes were prepared and assayed for endothelin converting enzyme activity as previously described (Biochem. Biophys. Res. Commun. 171 1291 (1990)).

HPLC Fractionation on Mono O

Rat lung plasma membranes (400 mg) were solubilized by stirring at 4° C. for 45 minutes in 50 ml of 20 mM Tris-HCl, pH 7.7 containing 2 mM dithiothreitol and 46 mM NOG (Buffer C). The unsolubilized materials were removed by centrifugation at 60,000×g for 30 minutes. Solubilized materials were injected onto a Mono Q HR 10/10 column (Pharmacia) and eluted with concentration gradients of 0–1M NaCl in 240 ml of Buffer C at 4 ml/minute. (Endothelin converting enzyme active fractions were eluted from 0.07 to 0.14 M NaCl). Absorbance at 280 nm was monitored by a LKB 2150 UVICORD SD monitor. Fractions were analyzed for endothelin converting enzyme activity and by SDS-PAGE. Protein content was determined by the Bio-Rad Protein Assay kit.

HPLC Fractionation on Superose 12

Mono Q fractions containing endothelin converting enzyme activity were pooled, concentrated to 25 mg/ml by Amicon Macrosolute Concentrators, and then a 200 µl sample was applied to Superose 12 (Pharmacia). Buffer B (100mM NaCl, 50 mM Hepes, pH 7.4) was used as the mobile phase. The flow rate was 0.3 ml/minute and 0.6 ml/fraction was collected. Protein standards of known molecular mass and blue dextran were chromatographed in parallel. Absorbance at 280 nm was monitored as above. Fractions were assayed for endothelin converting enzyme acitivity. Fractions containing endothelin converting enzyme activity were concentrated and analyzed by SDS-PAGE.

HPLC Fractionation on Mono P

Superose 12 fractions containing endothelin converting enzyme activity were pooled and passed through PD-10 columns (Pharmacia) to change to the starting buffer (25 mM bis-Tris, pH 6.9 by $CH_3COOH$). Samples were injected onto a Mono P HR 5/20 column (Pharmacia). After washing with the starting buffer, the column was eluted with a buffer containing 9.5% of Polybuffer 96 and 0.5% of Polybuffer 74 (both Pharmacia) adjusted to pH 5.9 by acetic acid. Values of pH in each fraction were determined. Absorbance at 280 nm was monitored. Fractions were assayed for endothelin converting enzyme activity

SDS-PAGE

Proteins were resolved by PhastGels (SDS-PAGE: 8-25 gradient; Isoelectric focusing: pH 5-8) in a Pharmacia Phastsystem. Gels were visualized by silver stain.

The enzyme has an apparent molecular mass of 90 KD as estimated by SDS-PAGE or gel filtration and appears to be a single peptide protein. (Boiling the sample resulting from Mono Q purification under reducing conditions did not change the results of the SDS-PAGE analysis). The enzyme may exist as isozymes with pIs at 6.2 and 6.3. The endothelin converting enzyme activity after Mono Q purification was found to be optimal at pH 3.5 at 37° C. The endothelin converting enzyme activity in active Mono Q fractions was inhibited by pepstatin A with an $IC_{50}$ of 5 nM. The endothelin converting enzyme activity of solubilized endothelin converting enzyme (P3 from rat lung) is not inhibited at 40 mM by TLCK, aprotinin, PMSF, E-64, bestatin, phosphoramidon or thiorphan. The endothelin converting enzyme activity of active Mono Q fractions was stimulated by divalent metal cations in the order of $Mn^{+2} \geq Zn^{+2} > Ca^{+2} > Mg^{+2} \geq Ba^{+2} = Co^{+2}$.

The ability of the compounds of the invention to inhibit a pepstatin A-inhibitable endothelin converting enzyme can be determined according to the following assay.

ECE Inhibitor Screening Assay

In a 1.5 mL tube, an assay cocktail containing 50 mM HEPES-100 mM NaCl buffer (pH 7.4 and containing 0.01% $NaN_3$), $MnCl_2$ (40 µM), pepstatin A (1 nM), Bestatin (40 µM), PMSF (40 µM), test compound (100 µM in DMSO) and solubilized endothelin converting enzyme (P3 from rat lung, see Biochem. Biophys. Res. Commun. 171 1291 (1990)) were added and vortexed. The above mixture without the test compound was used as the control.

Following a 15 minute preincubation at 37° C., benzyl succinate (100 µM), NaOAc, and Big ET (3 µg) were added. The mixture was incubated for 30 minutes at 37° C., followed by addition of pepstatin (40 µM) and 10% TFA to stop the reaction. The mixture was vortexed, centrifuged and the supernatant retained for HPLC determination of Big ET, ET-1 and CTF. The ET peaks were detected using absorbance at 226 nM. Percent inhibiton calculations were made with reference to controls based on quantitation of the ET-1 and Big ET peaks at the end of the incubation period. Table 1 shows the $IC_{50}$ (concentration at which the test compound inhibits enzyme activity by 50%) values for representative compounds of the invention.

TABLE 1

| Inhibition of Endothelin Converting Enzyme | |
|---|---|
| Compound of Example | $IC_{50}$ (nM) |
| 1 | 50 |
| 6 | 57 |
| 7 | 68 |
| 8 | 39 |
| 12 | 19 |
| 13 | 17 |
| 14 | 8 |
| 15 | 47 |
| 16 | 30 |
| 23 | 24 |
| 24 | 7 |
| 25 | 17 |
| 26 | 7 |
| 27 | 29 |
| 28 | 9 |
| 30 | 3 |
| 33 | 33 |
| 34 | 19 |
| 35 | 17 |
| 39 | 9.5 |
| 40 | 10 |
| 41 | 18 |
| 42 | 16 |
| 43 | 6 |
| 44 | 21 |
| 45 | 51 |
| 46 | 4 |
| 47 | 20 |
| 48 | 7 |
| 49 | 6 |
| 50 | 4 |
| 51 | 4 |
| 52 | 10 |
| 53 | 3 |
| 54 | 5 |
| 55 | 5 |

The data indicate that the compounds inhibit endothelin converting enzyme.

The ability of the compounds of the invention to lower blood pressure can be demonstrated according to the methods described in Matsumura, et al., Eur. J. Pharmacol. 185 103 (1990) and Takata, et al., Clin. Exp. Pharmacol. Physiol. 10 131 (1983).

The ability of the compounds of the invention to treat congestive heart failure can be demonstrated according to the method described in Margulies, et al., Circulation 82 2226 (1990).

The ability of the compounds of the invention to treat myocardial infarction can be demonstrated according to the method described in Watanabe, et al., Nature 344 114 (1990).

The ability of the compounds of the invention to treat coronary angina can be demonstrated according to the method described in Heistad, et al., Circ. Res. 54 711 (1984).

The ability of the compounds of the invention to treat cerebral vasospasm can be demonstrated according to the method described in Nakagomi, et al., J. Neurosurg. 66 915 (1987).

The ability of the compounds of the Invention to treat acute renal failure can be demonstrated according to the method described in Kon, et al., J. Clin. Invest. 83 1762 (1989).

The ability of the compounds of the invention to treat gastric ulceration can be demonstrated according to the method described in Wallace, et al., A/n. J. Physiol. 256 G661 (1989).

The ability of the compounds of the invention to treat cyclosporin-induced nephrotoxicity can be demonstrated according to the method described in Kon, et al., Kidney Int. 37 1487 (1990).

The ability of the compounds of the invention to treat endotoxin-induced toxicity (shock) can be demonstrated according to the method described in Takahashi, et al., Clinical Sci. 79 619 (1990).

The ability of the compounds of the invention to treat asthma can be demonstrated according to the method described in Potvin and Varma, Can. J. Physiol. and Pharmacol. 67 1213 (1989).

The ability of the compounds of the invention to treat atherosclerosis can be demonstrated according to the methods described in Bobik, et al., Am. J. Physiol. 258 C408 (1990) and Chobanian, et al., Hypertension 15 327 (1990).

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentane-propionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenyl-propionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The compounds of the present invention can also be used in the form of esters. Examples of such esters include a hydroxyl-substituted compound of formula I, II or III which has been acylated with a blocked or un-blocked amino acid residue, a phosphate function, a hemisuccinate residue, or an acyl residue of the formula RC(O)— or RC(S)— wherein R** is hydrogen, loweralkyl, haloalkyl, alkoxy, thioalkoxy or haloalkoxy. The amino acid esters of particular interest are glycine and lysine; however, other amino acid residues can also be used, including those wherein the amino acyl group is —C(O)CH$_2$NR$_{200}$R$_{201}$ wherein R$_{200}$ and R$_{201}$ are independently selected from hydrogen and loweralkyl or the group —NR$_{200}$R$_{201}$ forms a nitrogen containing heterocyclic ring. These esters serve as prodrugs of the compounds of the present invention and serve to increase the solubility of these substances in the gastrointestinal tract. These esters also serve to increase solubility for intravenous administration of the compounds. The prodrugs of this invention are metabolized in vivo to provide the hydroxyl-substituted compound of formula I, II or III. The preparation of the prodrug esters is carried out by reacting a hydroxyl-substituted compound of formula I, II or III with an activated amino acyl, phosphoryl, hemisuccinyl or acyl derivative as defined above. The resulting product is then deprotected to provide the desired pro-drug ester.

The compounds of the invention are useful for inhibiting pepstatin A-inhibitable endothelin converting enzyme in a human or other mammal. The compounds of the present invention are also useful for suppressing production of endothelin in a human or other mammal. In addition, the compounds of the present invention are useful for-the treatment or hypertension, congestive heart failure, myocardial infarction, reperfusion injury, coronary angina, cerebral vasospasm, acute renal failure, non-steroidal antiinflammatory drug induced gastric ulceration, cyclosporin-induced nephrotoxicity, endotoxin-induced toxicity, asthma and atherosclerosis in a human or other mammal.

Total daily dose administered to a host in single or divided doses may be in amounts, for example, from 0.001 to 1000 mg/kg body weight daily and more usually 1 to 500 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they can also be used in combination with one or more cardiovascular agents independently selected from diuretics, adrenergic blocking agents, vasodilators, calcium channel blockers, renin inhibitors, angiotensin converting enzyme (ACE) inhibitors, angiotensin II antagonists, potassium channel activators and other cardiovascular agents.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative renin inhibitors include enalkiren, RO 42-5892, PD-134672 and the like or a pharmaceutically acceptable salt thereof.

Representative angiotensin II antagonists include DUP 753 and the like.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compounds of the invention and the antihypertensive agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are Obvious to one skilled in the art are intended to be within the scope and nature of the invention which are defined in the appended claims.

What is claimed is:

1. A method for inhibiting endothelin converting enzyme comprising administering to a mammal in need of such treatment a therapeutically effective amount of a compound of the formula:

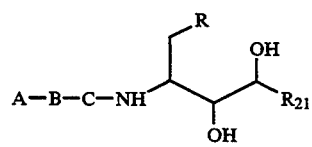

wherein

A is acetyl, pivaloyl, t-butyloxycarbonyl, benzyloxycarbonyl or phenylsulfonyl; or A is $HO_2C(CH_2)_n$-$C(O)$— wherein n is 1 to 3; or A is $R_{1a}C(O)$— or $R_{1a}S(O)_2$— wherein $R_{1a}$ is morpholinyl, piperazinyl or piperazinyl substituted with loweralkyl; or A is (aminoalkyl)(alkyl)aminocarbonyl, (alkylaminoalkyl)(alkyl)aminocarbonyl or (dialkylaminoalkyl)(alkyl)aminocarbonyl;

B is —N(R$_4$)CH(R$_3$)C(O)— wherein R$_4$ is hydrogen or loweralkyl and R$_3$ is cycloalkyl;

C is —N(R$_5$)CH(R$_6$)C(O)— wherein R$_5$ is hydrogen or loweralkyl and R$_6$ is loweralkyl;

R is naphthyl or indolyl; and

R$_{21}$ is loweralkyl; or a pharmaceutically acceptable salt, ester or prodrug thereof.

2. The method of claim 1 wherein R$_6$ is 2-butyl, R$_3$ is cyclohexylmethyl and R$_{21}$ is isobutyl.

3. A method for suppressing endothelin production comprising administering to a mammal in need of such treatment a therapeutically effective amount of a compound of the formula:

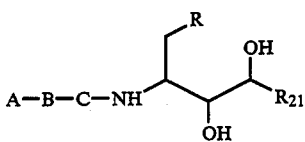

wherein

A is acetyl, pivaloyl, t-butyloxycarbonyl, benzyloxycarbonyl or phenylsulfonyl; or A is HO$_2$C(CH$_2$)$_n$-C(O)— wherein n is 1 to 3; or A is R$_{1a}$C(O)— or R$_{1a}$S(O)$_2$— wherein R$_{1a}$ is morpholinyl, piperazinyl or piperazinyl substituted with loweralkyl; or A is (aminoalkyl)(alkyl)aminocarbonyl, (alkylaminoalkyl)(alkyl)aminocarbonyl or (dialkylaminoalkyl)(alkyl)aminocarbonyl;

B is —N(R$_4$)CH(R$_3$)C(O)— wherein R$_4$ is hydrogen or loweralkyl and R$_3$ is cycloalkylalkyl;

C is —N(R$_5$)CH(R$_6$)C(O)— wherein R$_5$ is hydrogen or loweralkyl and R$_6$ is loweralkyl;

R is naphthyl or indolyl; and

R$_{21}$ is loweralkyl; or a pharmaceutically acceptable salt, ester or prodrug thereof.

4. The method of claim 3 wherein R$_6$ is 2-butyl, R$_3$ is cyclohexylmethyl and R$_{21}$ is isobutyl.

5. A compound of the formula:

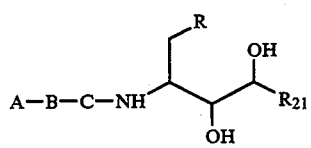

wherein

A is acetyl, pivaloyl, t-butyloxycarbonyl, benzyloxycarbonyl or phenylsulfonyl; or A is HO$_2$C(CH$_2$)$_n$-C(O)— wherein n is 1 to 3; or A is R$_{1a}$C(O)— or R$_{1a}$S(O)$_2$— wherein R$_{1a}$ is morpholinyl, piperazinyl or piperazinyl substituted with loweralkyl; or A is (aminoalkyl)(alkyl)aminocarbonyl, (alkylaminoalkyl)(alkyl)aminocarbonyl or (dialkylaminoalkyl)(alkyl)aminocarbonyl;

B is —N(R$_4$)CH(R$_3$)C(O)— wherein R$_4$ is hydrogen or loweralkyl and R$_3$ is cycloalkylalkyl;

C is —N(R$_5$)CH(R$_6$)C(O)— wherein R$_5$ is hydrogen or loweralkyl and R$_6$ is loweralkyl;

R is naphthyl or indolyl; and

R$_{21}$ is loweralkyl; or a pharmaceutically acceptable salt, ester or prodrug thereof.

6. The compound of claim 5 wherein R$_6$ is 2-butyl, R$_3$ is cyclohexylmethyl and R$_{21}$ is isobutyl.

7. A method for treating hypertension comprising administering to a mammal in need of such treatment a therapeutically effective amount of a compound of claim 5.

8. A compound selected from the group consisting of:
(2S,3R,4S)-2-(N-Boc-Cyclohexylalanyl-Isoleucyl-Amino)-1-(2-naphthyl-3,4-dihydroxy-6-methylheptane;
(2S,3R,4S)-2-(N-Boc-Cyclohexylalanyl-Isoleucyl-Amino)-1-(1-naphthyl-3,4-dihydroxy-6-methylheptane;
(2S,3R,4S)-2-(N-Boc-Cyclohexylalanyl-Isoleucyl-Amino)-1-(3-indolyl-3,4-dihydroxy-6-methylheptane;
(2S,3R,4S)-2-{(N-(4-Methylpiperazin-1-yl-carbonyl)-Cyclohexylalanyl-Isoleucyl)amino}-1-(2-naphthyl)-3,4-dihydroxy-6-methylheptane;
(2S,3R,4S)-2-{(N-Succinyl-Cyclohexylalanyl-Isoleucyl)amino}-1-(2-naphthyl)-3,4-dihydroxy-6-methylheptane;
(2S,3R,4S)-2-{(N-Acetyl-Cyclohexylalanyl-Isoleucyl)amino}-1-(2-naphthyl)-3,4-dihydroxy-6-methylheptane;
(2S,3R,4S)-2-{(N-(Morpholin-1-yl-carbonyl)-Cyclohexylalanyl-Isoleucyl)amino}-1-(2-naphthyl)-3,4-dihydroxy-6-methylheptane;
(2S,3R,4S)-2-{({N-(N,N-Dimethylaminoethyl)-N-methylamino}carbonyl-Cyclohexylalanyl-Isoleucyl)amino}-1-(2-naphthyl)-3,4-dihydroxy-6-methylheptane; and
(2S,3R,4S)-2-{(N-(4-Methylpiperazin-1-yl-sulfonyl)-Cyclohexylalanyl-Isoleucyl)amino}-1-(2-naphthyl)-3,4-dihydroxy-6-methylheptane; or a pharmaceutically acceptable salt, ester or prodrug thereof.

* * * * *